United States Patent
Itoh

(10) Patent No.: US 9,871,216 B2
(45) Date of Patent: Jan. 16, 2018

(54) ORGANIC PHOTOELECTRIC CONVERSION ELEMENT AND ORGANIC SOLAR CELL USING THE SAME

(75) Inventor: Hiroaki Itoh, Hachioji (JP)

(73) Assignee: KONICA MINOLTA, INC., Tokyo (JP)

(\*) Notice: Subject to any disclaimer, the term of this patent is extended or adjusted under 35 U.S.C. 154(b) by 741 days.

(21) Appl. No.: 14/237,850

(22) PCT Filed: Aug. 6, 2012

(86) PCT No.: PCT/JP2012/069986
§ 371 (c)(1),
(2), (4) Date: Feb. 7, 2014

(87) PCT Pub. No.: WO2013/021971
PCT Pub. Date: Feb. 14, 2013

(65) Prior Publication Data
US 2014/0190566 A1     Jul. 10, 2014

(30) Foreign Application Priority Data

Aug. 9, 2011   (JP) ................................. 2011-173672

(51) Int. Cl.
*H01L 51/42* (2006.01)
*C07D 311/74* (2006.01)
(Continued)

(52) U.S. Cl.
CPC ........ *H01L 51/4253* (2013.01); *C07D 277/04* (2013.01); *C07D 295/08* (2013.01);
(Continued)

(58) Field of Classification Search
CPC ............... Y02E 10/549; H01L 51/0043; H01L 51/0073; H01L 51/4253; H01L 51/0036;
(Continued)

(56) References Cited

U.S. PATENT DOCUMENTS 8,273,599 B2  9/2012  Bazan et al.
8,318,532 B2  11/2012  Bazan et al.
(Continued)

FOREIGN PATENT DOCUMENTS

JP   2008-293877   12/2008
JP   2009-126097    6/2009
(Continued)

OTHER PUBLICATIONS

International Preliminary Report on Patentability (IPRP) dated Feb. 20, 2014 (and English translation thereof) issued in International Application No. PCT/JP2012/069986.
(Continued)

*Primary Examiner* — Mayla Gonzalez Ramos
(74) *Attorney, Agent, or Firm* — Holtz, Holtz & Volek PC

(57) ABSTRACT

To provide an organic photoelectric conversion element whereby conversion efficiency is increased by morphology improvement in a power generation layer, and whereby short circuit current (Jsc) attenuation when irradiating light is simultaneously suppressed, and an organic solar cell using the same.

An organic photoelectric conversion element having: a transparent first electrode; a power generation layer having a p-type organic semiconductor material and an n-type organic semiconductor material; and a second electrode, on a transparent substrate, in which the power generation layer is a bulk heterojunction power generation layer including the p-type organic semiconductor material and the n-type organic semiconductor material, and additionally includes a compound represented by either the following general formula (I) or general formula (II).

(Continued)

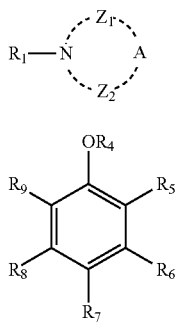

General formula (I)

General formula (II)

13 Claims, 2 Drawing Sheets

(51) Int. Cl.
*C07D 493/10* (2006.01)
*C07D 277/04* (2006.01)
*C07D 295/08* (2006.01)
*C07D 307/80* (2006.01)
*H01L 51/00* (2006.01)

(52) U.S. Cl.
CPC .......... *C07D 307/80* (2013.01); *C07D 311/74* (2013.01); *C07D 493/10* (2013.01); *H01L 51/0042* (2013.01); *H01L 51/0073* (2013.01); *Y02E 10/549* (2013.01)

(58) Field of Classification Search
CPC . H01L 51/0042; C07D 493/10; C07D 277/04; C07D 295/08; C07D 311/74; C07D 307/80
See application file for complete search history.

(56) References Cited

U.S. PATENT DOCUMENTS

| | | | |
|---|---|---|---|
| 2010/0130638 A1* | 5/2010 | Hanaki | C08K 5/45 523/137 |
| 2010/0282309 A1* | 11/2010 | Pschirer | B82Y 10/00 136/255 |
| 2011/0124808 A1* | 5/2011 | Akino | C07D 401/04 524/610 |
| 2012/0043529 A1 | 2/2012 | Uetani | |
| 2013/0240845 A1 | 9/2013 | Bazan et al. | |

FOREIGN PATENT DOCUMENTS

| | | |
|---|---|---|
| JP | 2010-080478 | 4/2010 |
| JP | 2010-512005 | 4/2010 |
| JP | 2011-119701 | 6/2011 |
| WO | WO 2008/066933 A2 | 6/2008 |

OTHER PUBLICATIONS

Hae Jung Son, et al.: "Synthesis of Fluorinated Polythienothiophene-co-benzodithiophenes and Effect of Fluorination on the Photovoltaic Properties", Journal of the American Chemical Society, 2011, 133, pp. 1885-1894 (in English).
International Search Report (ISR) dated Aug. 28, 2012 issued in International Application No. PCT/JP2012/069986.

\* cited by examiner

ORGANIC PHOTOELECTRIC CONVERSION ELEMENT AND ORGANIC SOLAR CELL USING THE SAME

TECHNICAL FIELD

The present invention relates to an organic photoelectric conversion element, more particularly, an organic photoelectric conversion element which can be used for an organic solar cell, and furthermore particularly, an organic photoelectric conversion element having both power generation performance and element durability, and an organic solar cell using the same.

BACKGROUND ART

An organic solar cell (organic photoelectric conversion element) has a power generation layer containing a p-type semiconductor and an n-type semiconductor on a transparent electrode, and a charge transport layer that transports generated charges to an electrode, and it has a configuration enabling that excitons formed by light absorption is charge-separated before deactivation and the generated charges are efficiently extracted to an electrode. In recent years, the efficiency has been significantly improved.

Further, as being producible by film formation of a solution containing organic substances using a simple method such as a coating method or a printing method, the organic solar cell is believed to be most appropriate for roll-to-roll mass production, and it is referred to as a next-generation solar cell that is expected to result in dramatic drop in cost compared to a solar cell of the related art.

However, compared to a crystal Si type solar cell or a solar cell consisting of a thin film of an inorganic semiconductor, the organic solar cell is still insufficient in terms of the power generation efficiency, and there is a problem that the aforementioned cost merit is not yet to be exhibited.

In addition, similar to a common organic electronic device (for example, OTFT or OLED), element lifetime of the organic solar cell is significantly impaired as it is affected by oxygen, moisture, and thus a barrier member (generally, a barrier film) which not allowing permeation of oxygen, moisture is needed. In particular, a problem is caused by incorporation of oxygen that lifetime of an organic solar cell is significantly impaired as an attenuation in short circuit current (Jsc) accompanied with decomposition of organic substances occurs according to continuous light irradiation.

In relation to the aforementioned problem, a technique of improving conversion efficiency by adding at least one alkyl-containing molecule with low molecular weight to a solution of a p-type semiconductor conjugate polymer and an n-type semiconductor fullerene is disclosed (for example, Patent Literature 1). It is known that, according to the effect by those additives, light conductivity and a charge transport property are improved by morphology improvement of a bulk heterojunction layer, which is formed of a p-type semiconductor conjugate polymer and an n-type semiconductor fullerene (hereinbelow, also referred to as a power generation layer). Further, a technique of obtaining even higher conversion efficiency by adding a specific aromatic compound having a hydroxyl group and low molecular weight followed by coating and drying is disclosed (for example, Patent Literature 2). By adding those additives to a coating liquid, aggregation state of a polymer or fullerene is generally controlled, and thus it is expected to form more preferable morphology.

Further, to lower the oxygen effect, a technique which is by adding 1,4-diazabicyclo[2,2,2]octane (DABCO) as a singlet oxygen quencher to suppress discoloration caused by oxygen is disclosed (for example, Non-Patent Literature 1).

CITATION LIST

Patent Literature

Patent Literature 1: JP-T-2010-512005
Patent Literature 2: JP-A-2010-80478

Non-Patent Literature

Non-Patent Literature 1: J. Am. Chem. Soc., 2011, 133, 1885-1894

SUMMARY OF INVENTION

Technical Problem

However, as a result of intensive studies, the inventors found a problem that, as the additives generally have high melting point or are present as a solid at room temperature, they stay in a power generation layer and become a factor for causing an impairment of lifetime of a solar cell.

Further, according to the aforementioned published technique, the effect against a problem associated with short circuit current attenuation caused by continuous light irradiation as described above is not shown, and a technique for obtaining both conversion efficiency and element durability at the time of light irradiation by additives has not been obtained.

A object of the present invention is to provide an organic photoelectric conversion element whereby conversion efficiency is increased by morphology improvement in a power generation layer, and whereby short circuit current (Jsc) attenuation when irradiating light is simultaneously suppressed, and an organic solar cell using the same.

Solution to Problem

The aforementioned object of the present invention can be achieved by the following configurations.

1. An organic photoelectric conversion element including: a transparent first electrode; a power generation layer having a p-type organic semiconductor material and an n-type organic semiconductor material; and a second electrode, on a transparent substrate, in which the power generation layer is a bulk heterojunction power generation layer including the p-type organic semiconductor material and the n-type organic semiconductor material, and additionally includes a compound represented by either general formula (I) or general formula (II) shown below:

[Chemical formula 1]

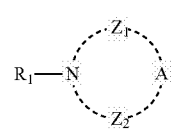

General formula (I)

Wherein $R_1$ represents a substituted or unsubstituted aryl group, $Z_1$ and $Z_2$ each represents a substituted or unsubstituted alkylene group having 1 to 3 carbon atoms, provided that sum of the carbon atoms in the alkylene group represented by $Z_1$ and $Z_2$ is 3 to 6. A represents an oxygen atom, $N-Z_3$, or $S(O)_{n5}$, and $Z_3$ represents an alkyl group or an aryl group. n5 represents an integer of from 0 to 2.

[Chemical formula 2]

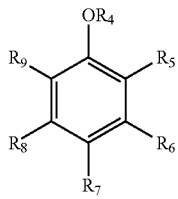

General formula (II)

Wherein $R_4$ represents a hydrogen atom, or a substituted or unsubstituted alkyl group, or a substituted or unsubstituted trialkylsilyl group, $R_5$, $R_6$, $R_7$, $R_8$ and $R_9$ each independently represents a hydrogen atom, a substituted or unsubstituted alkyl group, a substituted or unsubstituted alkoxy group, a substituted or unsubstituted aryl group, a substituted or unsubstituted aryloxy group, a substituted or unsubstituted alkenyl group, a substituted or unsubstituted alkenyloxy group, a substituted or unsubstituted acylamino group, a halogen atom, a substituted or unsubstituted alkylthio group, a substituted or unsubstituted arylthio group, a substituted or unsubstituted alkoxycarbonyl group, a substituted or unsubstituted acyloxy group, a substituted or unsubstituted acyl group, a substituted or unsubstituted sulfonamide group, a substituted or unsubstituted trialkylsilyl group, a substituted or unsubstituted heterocyclic ring, a substituted or unsubstituted fused ring, or a combination thereof. It is also possible that two groups among $R_4$ to $R_9$ may be linked to each other to form a substituted or unsubstituted 5- to 6-membered ring.

2. The organic photoelectric conversion element described in above 1, in which the general formula (I) is represented by any one of the following general formulas (I-A) to (I-E):

[Chemical formula 3]

General formula (I-A)

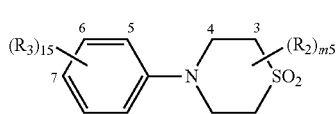

[Chemical formula 4]

General formula (I-B)

[Chemical formula 5]

General formula (I-C)

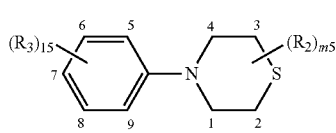

[Chemical formula 6]

General formula (I-D)

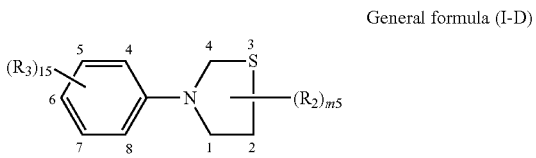

[Chemical formula 7]

General formula (I-E)

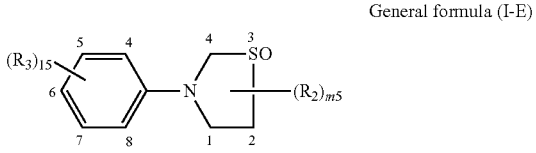

Wherein $R_2$ and $R_3$ represent a halogen atom, a substituted or unsubstituted alkyl group ($-R_a$), a hydroxyalkyl group ($-R_a(OH)$), an alkoxy group ($-OR_a$), an aryloxy group, an amino group ($-NH_2$, $-NHR_a$, $-N(R_a)_2$), a thioether group ($-SR_a$), an ester group, $-COR_a$, $-COOR_a$, $-NHCOR_a$, $-NHCOOR_a$, $-NHSO_2R_a$, or an alkylcarbonyloxy group ($-OCOR_a$), in which $R_a$ represents a substituted or unsubstituted alkyl group having 1 to 20 carbon atoms or a substituted or unsubstituted aryl group having 6 to 20 carbon atoms, and m5 and 15 represent an integer of from 0 to 4.

3. The organic photoelectric conversion element described in above 1, in which the general formula (II) is represented by the following general formula (II-A):

[Chemical formula 8]

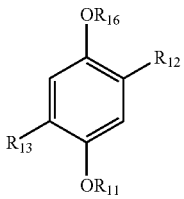

General formula (II-A)

In general formula (II-A), $R_{10}$ to $R_{13}$ each independently represents a hydrogen atom or a substituted or unsubstituted alkyl group, in which $R_{11}$ and $R_{13}$ may be linked to each other to form a substituted or unsubstituted 5- to 6-membered ring.

4. An organic solar cell having the organic photoelectric conversion element described in any one of the above 1 to 3, in which the solubility parameter (SP value) of the compound represented by the general formula described in any one of the above 1 to 3 is form 19 to 23.

Advantageous Effects of Invention

According to the present invention, an organic photoelectric conversion element whereby conversion efficiency is increased by morphology improvement in a power generation layer, and whereby short circuit current (Jsc) attenuation when irradiating light is simultaneously suppressed, and an organic solar cell using the same can be provided.

DESCRIPTION OF EMBODIMENTS

The present invention can provide an organic photoelectric conversion element and an organic solar cell using the same, in which the organic photoelectric conversion element has, on a transparent substrate, a transparent first electrode; a power generation layer having a p-type organic semiconductor material and an n-type organic semiconductor material; and a second electrode, the power generation layer is a bulk heterojunction power generation layer including the p-type organic semiconductor material and the n-type organic semiconductor material, and additionally includes a compound represented by the above general formula (I) or general formula (II) (hereinbelow, also referred to as an antioxidant), and as the aforementioned compound is included in the power generation layer, the conversion efficiency can be increased by morphology improvement in the power generation layer, and also at the same time, short circuit current (Jsc) attenuation when irradiating light can be suppressed.

(Configuration of Organic Photoelectric Conversion Element)

Figure 1:
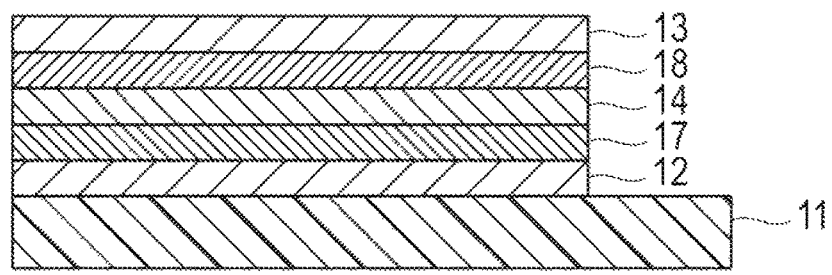
FIG. 1 is a drawing exemplifying a photoelectric conversion element of the present invention.

FIG. 1 is a schematic drawing illustrating an exemplary configuration of a photoelectric conversion element of the present invention.

The organic photoelectric conversion element 10 includes the transparent first electrode 12 on the transparent substrate 11, the power generation layer 14 on the first electrode 12, and the second electrode 13 on the power generation layer 14.

In the example of FIG. 1, the hole transport layer 17 explained below is present between the first electrode 12 and the power generation layer 14, and the electron transport layer 18 explained below is present between the power generation layer 14 and the second electrode 13.

According to the present invention, the transparent substrate 11 and the first electrode 12 are transparent and the light used for photoelectric conversion enters from the transparent substrate 11 and the first electrode. 12 and reaches the power generation layer 14 in FIG. 1.

The power generation layer 14 is a layer for converting light energy into electric energy and it contains a p-type organic semiconductor material and an n-type organic semiconductor material.

The p-type organic semiconductor material correspondingly functions as an electron donor (donor) and the n-type organic semiconductor material correspondingly functions as an electron acceptor (acceptor).

As described herein the electron donor and the electron acceptor indicate "an electron donor and an electron acceptor which form a pair of hole and electron (charge separation state) as a result of transfer of electrons from the electron donor to the electron acceptor at the time of light absorption", and instead of simple donating or accepting electrons like an electrode, they donate or accept electrons according to a photoreaction.

In FIG. 1, the light entering from the first electrode 12 via the transparent substrate 11 is absorbed by the electron acceptor or the electron donor in the power generation layer 14 of the power generation layer 14 and, as the electrons are transferred from the electron donor to the electron acceptor, a pair of hole and electron (charge separation state) is formed.

The generated charges pass through an internal electric field, for example, when work function is different between the first electrode 12 and the second electrode 13, electrons pass through electron acceptors and holes pass through electron donors due to a potential difference between the first electrode 12 and the second electrode 13, and each of them are transferred to a different electrode, and thus photoelectric current is detected.

In the example of FIG. 1, work function of the first electrode 12 is larger than work function of the second electrode 13, and thus the holes are transported to the first electrode 12 and the electrons are transported to the second electrode 13. In such case, for the second electrode 13, an easily oxidizable metal as having small work function is used. In such case, the first electrode functions as an anode (positive electrode) and the second electrode functions as a cathode (negative electrode).

Figure 2:
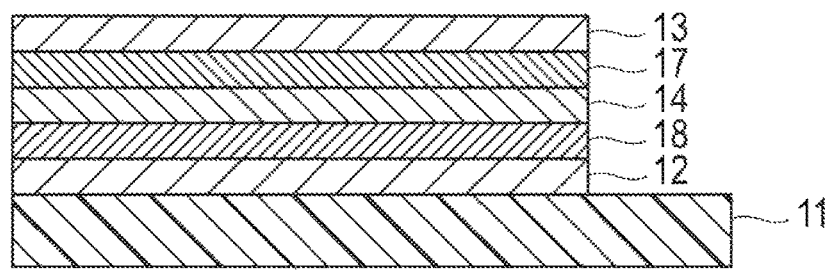
FIG. 2 is a schematic cross-sectional drawing illustrating another exemplary configuration of an organic photoelectric conversion element of the present invention.

Another exemplary configuration is shown in FIG. 2.

In FIG. 2, contrary to the case of FIG. 1, a case in which it is designed such that, as a work function of the second electrode 13 is larger than a work function of the first electrode 12, the electrons are transported to the first electrode 12 and the holes are transported to the second electrode 13 is shown. In such case, the electron transport layer 18 is present between the first electrode 12 and the power generation layer 14 and the hole transport layer 17 described below is present between the power generation layer 14 and the second electrode 13, and the first electrode functions a cathode (negative electrode) and the second electrode functions as an anode (positive electrode).

From the viewpoint of durability, the configuration shown in FIG. 2 in particular, i.e., a configuration in which the first electrode is a cathode (negative electrode) and the second electrode is an anode (positive electrode), is a preferred embodiment of the present invention.

In addition, although not shown in FIG. 1 and FIG. 2, the organic photoelectric conversion element of the present invention may also include a layer such as a hole blocking layer, an electron blocking layer, an electron injection layer, a hole injection layer, or a smoothing layer, and the like.

Figure 3:
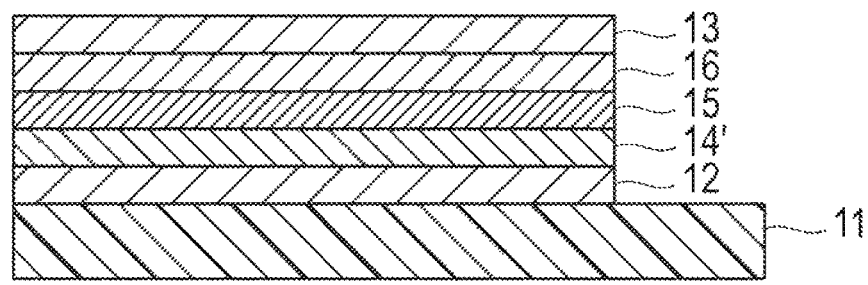
FIG. 3 is a schematic cross-sectional drawing illustrating an exemplary organic photoelectric conversion element of the present invention which is equipped with a tandem type power generation layer.

Further, for the purpose of improving utilization ratio of sun light (i.e., photoelectric conversion efficiency), it may also possible to include a tandem type configuration in which the photoelectric conversion elements are laminated. FIG. 3 is a cross-sectional drawing illustrating an organic photoelectric conversion element equipped with a tandem type power generation layer.

In a case of a tandem type configuration, after laminating the first electrode 12 and the first power generation layer 14' on the substrate 11 and laminating the charge recombination layer 15, a tandem type configuration can be obtained by laminating the second the power generation layer 16 and subsequently the second electrode 13.

The second the power generation layer 16 may be a layer which absorbs the same spectrum as the absorption spectrum of the first power generation layer 14' or a layer which absorbs a different spectrum. However, it is preferably a layer absorbing a different spectrum.

Further, although in a space between the first power generation layer 14' or the second the power generation layer 16 and each electrode, the hole transport layer 17 or the electron transport layer 18 may be present. However, in the present invention, it is preferable for each power generation layer to have the configuration shown in FIG. 2 even for the tandem configuration.

Hereinbelow, materials constituting those layers are explained.

<Antioxidant>

The present invention is characterized in that the power generation layer is a bulk heterojunction-type power generation layer having a p-type organic semiconductor material and an n-type organic semiconductor material, and it additionally contains a compound represented by the above general formula (I) or general formula (II) (hereinbelow, also referred to as an antioxidant). Specific examples of the antioxidant which may be preferably used in the present invention are illustrated. However, it is not limited thereto if the same effects are obtained from a compound. In the present invention, the power generation layer contains, as an antioxidant, a compound represented by the above general formula (I) or general formula (II), and thus it exhibits a function as an oxygen scavenger for quenching singlet oxygen.

The compound represented by general formula [I] of the present invention is explained.

In general formula [I], $R_1$ represents a substituted or unsubstituted aryl group, $Z_1$ and $Z_2$ each represents a substituted or unsubstituted alkylene group having 1 to 3 carbon atoms, provided that sum of the carbon atoms in the alkylene group represented by $Z_1$ and $Z_2$ is 3 to 6. A represents an oxygen atom, N—$Z_3$, or S(O)$_{n5}$, and $Z_3$ represents an alkyl group or an aryl group. n5 represents an integer of from 0 to 2.

Examples of the aryl group represented as $R_1$ include a phenyl group, a 1-naphthyl group, and a pyridinyl group, and those aryl groups may have a substituent group. Examples of the substituent group include an alkyl group having 1 to 20 carbon atoms (such as a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group), a cycloalkyl group having 4 to 20 carbon atoms (such as a cyclopentyl group and a cyclohexyl group), an alkenyl group having 2 to 20 carbon atoms (such as a vinyl group and an allyl group), an alkynyl group having 2 to 20 carbon atoms (such as an ethynyl group and a propargyl group), an aryl group having 6 to 20 carbon atoms (such as a phenyl group, an alkoxy-substituted phenyl group such as a 4-dodecyloxyphenyl group or a 4-(2-ethylhexyloxy)phenyl group, and a naphthyl group), an aromatic heterocyclic group having 3 to 20 carbon atoms (such as a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, and a phthalazinyl group), a heterocyclic group (such as a pyrrolidyl group, an imidazolidyl group, a morpholyl group, and an oxazolidyl group), an alkoxy group having 1 to 20 carbon atoms (such as a methoxy group, an ethoxy group, a propyloxy group, a butyloxy group, a pentyloxy group, a t-pentyloxy group, a hexyloxy group, a 2-ethylhexyloxy group, an octyloxy group, a t-octyloxy group, a decyloxy group, a dodecyloxy group, a tetradecyloxy group, and a hexadecyloxy group), a cycloalkoxy group having 4 to 20 carbon atoms (such as a cyclopentyloxy group and a cyclohexyloxy group), an aryloxy group having 6 to 20 carbon atoms (such as a phenoxy group and a naphthyloxy group), a hydroxyalkyl group having 1 to 20 carbon atoms (such as a hydroxymethyl group, a 2-hydroxyethyl group, and a 3-hydroxypropyl group), an alkylthio group having 1 to 20 carbon atoms (such as a methylthio group, an ethylthio group, a propylthio group, a butylthio group, a pentylthio group, a hexylthio group, an octylthio group, and a dodecylthio group), a cycloalkylthio group having 4 to 20 carbon atoms (such as a cyclopentylthio group and a cyclohexylthio group), an arylthio group having 6 to 20 carbon atoms (such as a phenylthio group and a naphthylthio group), an alkoxycarbonyl group having 1 to 20 carbon atoms (—COOR$_b$) (such as a methyloxycarbonyl group, an ethyloxycarbonyl group, a butyloxycarbonyl group, an octyloxycarbonyl group, and a dodecyloxycarbonyl group), an aryloxycarbonyl group having 6 to 20 carbon atoms (—COOAr$_b$) (such as a phenyloxycarbonyl group and a naphthyloxycarbonyl group), a sulfamoyl group (such as an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group), an acyl group having 2 to 20 carbon atoms (—COR$_b$) (such as an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group), an acyloxy group having 2 to 20 carbon atoms (—OCOR$_b$) (alkylcarbonyloxy group) (such as an acetyloxy group, an ethylcarbonyloxy group, a butylcarbonyloxy group, an octylcarbonyloxy group, a dodecylcarbonyloxy group, a tridecylcarbonyloxy group, and a phenylcarbonyloxy group), an amide group having 1 to 20 carbon atoms (—NHCOR$_b$) (such as a methylcarbonylamino group, an ethylcarbonylamino group, a dimethylcarbonylamino group, a propylcarbonylamino group, a pentylcarbonylamino group, a cyclohexylcarbonylamino group, a 2-ethyihexylcarbonylamino group, an octylcarbonylamino group, a dodecylcarbonylamino group, a phenylcarbonylamino group, and a naphthylcarbonylamino group), an alkoxycarbonylamino group having 1 to 20 carbon atoms (—NHCOOR$_b$) (such as a methoxycarbonylamino group, an ethoxycarbonylamino group, a propyloxycarbonylamino group, a pentyloxycarbonylamino group, a cyclohexyloxycarbonylamino group, a 2-ethylhexyloxycarbonylamino group, an octyloxycarbonylamino group, a dodecyloxycarbonylamino group, a phenoxycarbonylamino group, and a naphthyloxycarbonylamino group), an alkylsulfonylamino group having 1 to 20 carbon atoms (—NHSO$_2$—R$_b$) (a methylsulfonylamino group, an ethylsulfonylamino group, a butylsulfonylamino group, a cyclohexylsulfonylamino group, a 2-ethyihexylsulfonylamino group, a dodecylsulfonylamino group, and an octadecylsulfonylamino group), an arylsulfonylamino group having 6 to 20 carbon atoms (—NHSO$_2$—Ar$_b$) (a phenylsulfonylamino group, a naphthylsulfonylamino group, a 2-pyridylsulfonylamino group, and the like), a carbamoyl group having 1 to 20 carbon atoms (—CONH$_2$, —CONHR$_b$, or —CON(R$_b$)$_2$) (such as an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group), an ureido group having 1 to 20 carbon atoms (—NHCONH$_2$, —NHCONHR$_b$, or —NHCON(R$_b$)$_2$) (such as a methylureido group, an ethylureido group, a pentylureido group, a cyclohexylureido group, an octylureido group, a dodecylureido group, a phenylureido group, a naphthylureido group, and a 2-pyridylaminoureido group), a sulfinyl group having 1 to 20 carbon atoms (—S(=O)—$R_b$) (such as a methylsulfinyl group, an ethylsulfinyl group, a butylsulfinyl group, a cyclohexylsulfinyl group, a 2-ethyihexylsulfinyl group, a dodecylsulfinyl group, a phenylsulfinyl group, a naphthylsulfinyl group, and a 2-pyridylsulfinyl group), an alkylsulfonyl group (—S(=O)$_2$—$R_b$) (such as a methylsulfonyl group, an ethylsulfonyl group, a butylsulfonyl group, a cyclohexylsulfonyl group, a 2-ethylhexylsulfonyl group, and a dodecylsulfonyl group), an arylsulfonyl group having 6 to 20 carbon atoms (—S(=O)$_2$—$Ar_b$) (a phenylsulfonyl group, a naphthylsulfonyl group, and a 2 -pyridylsulfonyl group), an amino group having 0 to 20 carbon atoms (—$NH_2$, —$NHR_b$, or —$N(R_b)_2$) (such as an amino group, an ethylamino group, an ethyloctylamino group, a dimethylamino group, a butylamino group, a cyclopentylamino group, a 2-ethylhexylamino group, a dodecylamino group, an anilino group, a naphthylamino group, a 2-pyridylamino group, and a methyl (2-tetrahydrofuranyl) amino group), a halogen atom (such as a fluorine atom, a chlorine atom, and a bromine atom), a fluorohydrocarbon group having 1 to 20 carbon atoms (such as a fluoromethyl group, a trifluoromethyl group, a pentafluoroethyl group, and a pentafluorophenyl group), a cyano group, a nitro group, a hydroxyl group, a mercapto group, a silyl group (such as a trimethylsilyl group, a triisopropylsilyl group, a triphenylsilyl group, and a phenyldiethylsilyl group) (meanwhile, in the above, $R_b$ represents a substituted or unsubstituted alkyl group having 1 to 20 carbon atoms, or $Ar_b$ represents an aryl group having 6 to 20 carbon atoms). These substituent groups may be further substituted with a substituted or unsubstituted alkyl group or alkoxy group having 1 to 20carbon atoms, or a substituted or unsubstituted aryl group or aryloxy group having 6 to 20carbon atoms, and at that time, the substituent group is an alkyl group having 1 to 20carbon atoms.

Among them, a halogen atom, an alkyl group having 1 to 20 carbon atoms, an alkoxy group having 1 to 20 carbon atoms, a hydroxyalkyl group having 1 to 20 carbon atoms, or an amino group having 0 to 20 carbon atoms is preferrably. And an alkyl group having 1 to 20 carbon atoms, an alkoxy group having 1 to 20 carbon atoms, or an amino group having 0 to 20 carbon atoms is more preferrably.

$Z_1$ and $Z_2$ each represents a substituted or unsubstituted alkylene group having 1 to 3 carbon atoms, and sum of the alkylene group represented by $Z_1$ and $Z_2$ is 3 to 6. When the alkylene group is substituted, the same substituent groups as the substituent groups for the aryl group represented by $R_1$ can be employed. Among them, preferred is an alkyl group having 1 to 20 carbon atoms (such as a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group), a cycloalkyl group having 4 to 20 carbon atoms (such as a cyclopentyl group, and a cyclohexyl group), an alkenyl group having 2 to 20 carbon atoms (such as a vinyl group and an allyl group), an alkynyl group having 2 to 20 carbon atoms (such as an ethynyl group and a propargyl group), an aryl group having 6 to 20 carbon atoms (such as a phenyl group, an alkoxy-substituted phenyl group such as a 4-dodecyloxyphenyl group or a 4-(2-ethylhexyloxy)phenyl group, and a naphthyl group), an alkoxy group having 1 to 20 carbon atoms (such as a methoxy group, an ethoxy group, a propyloxy group, a butyloxy group, a pentyloxy group, a t-pentyloxy group, a hexyloxy group, a 2-ethylhexyloxy group, an octyloxy group, a t-octyloxy group, a decyloxy group, a dodecyloxy group, a tetradecyloxy group, and a hexadecyloxy group), a cycloalkoxy group having 4 to 20 carbon atoms (such as a cyclopentyloxy group and a cyclohexyloxy group), an aryloxy group having 6 to 20 carbon atoms (such as a phenoxy group and a naphthyloxy group), a hydroxyalkyl group having 1 to 20 carbon atoms (such as a hydroxymethyl group, a 2-hydroxyethyl group, and a 3-hydroxypropyl group), an alkylthio group having 1 to 20 carbon atoms (such as a methylthio group, an ethylthio group, a propylthio group, a butylthio group, a pentylthio group, a hexylthio group, an octylthio group, and a dodecylthio group).

A represents an oxygen atom, N—$Z_3$, or $S(O)_{n5}$, and it is preferably $S(O)_{n5}$. Further, examples of the alkyl group represented by $Z_3$ include a linear or branched alkyl group having 1 to 24 carbon atoms, and examples of the aryl group represented by $Z_3$ include a phenyl group, and each group of them may also have a substituent group. Preferred examples of the substituent group include an alkyl group or alkoxy group having 1 to 20 carbon atoms. n5 represents an integer of from 0 to 2, and it is preferably 2.

According to the present invention, it is preferable to use a compound represented by the general formulas (I-A) to (I-E) among general formula (I).

Among general formulas (I-A) to (I-E), $R_2$ and $R_3$ represent a halogen atom, a substituted or unsubstituted alkyl group (—$R_a$), a hydroxyalkyl group (—$R_a(OH)$), an alkoxy group (—$OR_a$), an aryloxy group, an amino group (—$NH_2$, —$NHR_a$, —$N(R_a)_2$), athioether group (—$SR_a$), an ester group, —$COR_a$, —$COOR_a$, —$NHCOR_a$, —$NHCOOR_a$, —$NHSO_2R_a$, or an alkylcarbonyloxy group (—$OCOR_a$), wherein $R_a$ represents a substituted or unsubstituted alkyl group having 1 to 20 carbon atoms or a substituted or unsubstituted aryl group having 6 to 20 carbon atoms, and m5 and l5 represent an integer of from 0 to 4. Meanwhile, the expression "substituted or unsubstituted" means that all of the aforementioned substituent groups may be substituted.

As for an alkyl group (—$R_a$), a hydroxyalkyl group (—$R_a(OH)$), an alkoxy group (—$OR_a$), an aryloxy group, an amino group (13 $NH_2$, —$NHR_a$, —$N(R_a)_2$), a thioether (—$SRa$) group, an ester group, —$COR_a$, —$COOR_a$, —$NHCOR_a$, —$NHCOOR_a$, —$NHSO_2R_a$, an alkylcarbonyloxy (—$OCOR_a$) group for $R_2$ and $R_3$, the same substituent groups as the substituent groups for the aryl group represented by $R_1$ can be employed.

Among them, preferred are an alkyl group having 1 to 20 carbon atoms (such as a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group), an aryl group having 6 to 20 carbon atoms (such as a phenyl group, an alkoxy-substituted phenyl group such as a 4-dodecyloxyphenyl group or a 4-(2-ethylhexyloxy)phenyl group, and a naphthyl group), an alkoxy group having 1 to 20 carbon atoms (such as a methoxy group, an ethoxy group, a propyloxy group, a butyloxy group, a pentyloxy group, a t-pentyloxy group, a hexyloxy group, a 2-ethylhexyloxy group, an octyloxy group, a t-octyloxy group, a decyloxy group, a dodecyloxy group, a tetradecyloxy group, and a hexadecyloxy group), an aryloxy group having 6 to 20 carbon atoms (such as a phenoxy group and a naphthyloxy group), a hydroxyalkyl group having 1 to 20 carbon atoms (such as a hydroxymethyl group, a 2-hydroxyethyl group, and a 3-hydroxypropyl group), an alkylthio group having 1 to 20 carbon atoms (such as a methylthio group, an ethylthio group, a propylthio group, a butylthio group, a pentylthio group, a hexylthio group, an octylthio group, and a dodecylthio group), an alkoxycarbonyl group having 1 to 20 carbon atoms (—COOR$_a$) (such as a methyloxycarbonyl group, an ethyloxycarbonyl group, a butyloxycarbonyl group, an octyloxycarbonyl group, and a dodecyloxycarbonyl group), an aryloxycarbonyl group having 6 to 20 carbon atoms (—COOR$_a$) (such as a phenyloxycarbonyl group and a naphthyloxycarbonyl group), an acyloxy group having 2 to 20 carbon atoms (—OCOR$_a$) (an alkylcarbonyloxy group) (such as an acetyloxy group, an ethylcarbonyloxy group, a butylcarbonyloxy group, an octylcarbonyloxy group, a dodecylcarbonyloxy group, a tridecylcarbonyloxy group, and a phenylcarbonyloxy group), an amide group having 1 to 20 carbon atoms (—NHCOR$_a$) (such as a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group), an alkoxycarbonylamino group having 1 to 20 carbon atoms (—NHCOOR$_a$) (such as a methoxycarbonylamino group, an ethoxycarbonylamino group, a propyloxycarbonylamino group, a pentyloxycarbonylamino group, a cyclohexyloxycarbonylamino group, a 2-ethylhexyloxycarbonylamino group, an octyloxycarbonylamino group, a dodecyloxycarbonylamino group, a phenoxycarbonylamino group, and a naphthyloxycarbonylamino group), an alkylsulfonylamino group having 1 to 20 carbon atoms (—NHSO$_2$—R$_a$) (a methylsulfonylamino group, an ethylsulfonylamino group, a butylsulfonylamino group, a cyclohexylsulfonylamino group, a 2-ethylhexylsulfonylamino group, a dodecylsulfonylamino group, and an octadecylsulfonylamino group), an arylsulfonylamino group having 6 to 20 carbon atoms (—NHSO$_2$—R$_a$) (a phenylsulfonylamino group, a naphthylsulfonylamino group, and a 2-pyridylsulfonylamino group), an amino group having 0 to 20 carbon atoms (—NH$_2$, —NHR$_a$, or —N(R$_a$)$_2$) (such as an amino group, an ethylamino group, an ethyloctylamino group, a dimethylamino group, a butylamino group, a cyclopentylamino group, a 2-ethylhexylamino group, a dodecylamino group, an anilino group, a naphthylamino group, a 2-pyridylamino group, a methyl (2-tetrahydrofuranyl)amino group), and a halogen atom (such as a fluorine atom, a chlorine atom, and a bromine atom). These substituent groups may be further substituted with a substituted or unsubstituted alkyl group or alkoxy group having 1 to 20 carbon atoms or a substituted or unsubstituted aryl group or aryloxy group having 6 to 20 carbon atoms, and at that time, the substituent group is an alkyl group having 1 to 20 carbon atoms.

More preferably, in general formulas (I-A) to (I-E), R$_2$ and R$_3$ represent an alkyl group, an alkoxy group, an amino group, a thioether group, an ester group, or an alkylcarbonyloxy group, and among them, an alkoxy group having 1 to 20 carbon atoms is more preferable.

m5 and l5 represent an integer of from 0 to 4, preferably an integer of from 0 to 2. m5 is more preferably 0 and l5 is more preferably 1.

Further, R$_3$ is preferably substituted such that it is present on a para position of benzene ring (i.e., para position relative to a "nitrogen-containing ring" substituted group).

Hereinbelow, specific examples of the compound of general formula (I) are explained, but the present invention is not limited to them.

[Chemical formula 9]

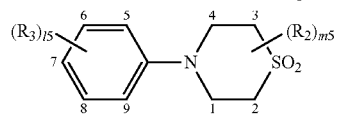

| Compound | R$_2$ | m5 | R$_3$ | l5 |
|---|---|---|---|---|
| I-1 | — | 0 | —OCH$_3$ (7) | 1 |
| I-2 | — | 0 | —OC$_9$H$_{17}$ (7) | 1 |
| I-3 | — | 0 | —OC$_2$H$_5$ (7) | 1 |
| I-4 | — | 0 | —OC$_4$H$_9$ (7) | 1 |
| I-5 | — | 0 | —OC$_6$H$_{13}$ (7) | 1 |
| I-6 | — | 0 | —OC$_{10}$H$_{21}$ (7) | 1 |
| I-7 | — | 0 | —OC$_{16}$H$_{33}$ (7) | 1 |
| I-8 | — | 0 | —OCH$_3$ (6,8) | 2 |
| I-9 | — | 0 | —N(C$_2$H$_5$)(C$_8$H$_{17}$) (7) | 1 |
| I-10 | — | 0 | —OC$_{12}$H$_{25}$ (7); —Cl (6) | 2 |
| I-11 | — | 0 | —O—C(=O)—C$_{13}$H$_{27}$ (7) | 1 |
| I-12 | — | 0 | —OC$_{12}$H$_{25}$ (7) | 1 |
| I-13 | — | 0 | —NHCOOC$_{12}$H$_{25}$ (5) | 1 |
| I-14 | —CH$_3$ | (1,1,4,4) 4 | —OC$_{12}$H$_{25}$ (7) | 1 |
| I-15 | —CH$_3$ | (2,2,3,3) 4 | —OC$_{16}$H$_{33}$ (7) | 1 |
| I-16 | — | 0 | —OC$_{12}$H$_{25}$ (5) | 1 |
| I-17 | — | 0 | —OCH$_2$—C$_6$H$_5$ (7) | 1 |
| I-18 | — | 0 | —NHSO$_2$C$_{18}$H$_{37}$ (5) | 1 |
| I-19 | —CH$_2$OH | (1) 1 | —O—C(=O)—C$_{13}$H$_{27}$ (7) | 1 |
| I-20 | —CH$_3$ | (2,2,3,3) 4 | —OC$_{12}$H$_{25}$ (7) | 1 |

[Chemical formula 10]

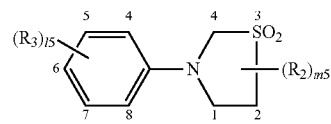

| Compound | R₂ | m5 | R₃ | | l5 |
|---|---|---|---|---|---|
| I-21 | — | 0 | —OC₁₄H₂₉ | (6) | 1 |
| I-22 | — | 0 | —OC₂H₆ | (5,7) | 2 |
| I-23 | — | 0 | —NHSO₂—C₆H₄—OC₁₂H₂₅ | (7) | 1 |
| I-24 | —OC₂H₅ | (1) | 1 | —OC₁₂H₂₅ | (5) | 1 |
| I-25 | —CH₃ | (3,3) | 2 | —OCH₂—C₆H₅ | (7) | 1 |

I-26

C₁₂H₂₅O—C₆H₄—N(CH₂CH₂)₂SO₂ (7-membered ring with SO₂)

I-27

C₁₂H₂₅O—C₆H₄—N(CH₂)₃SO₂(CH₂)₃ (8-membered ring with SO₂)

I-28

C₁₂H₂₅O—C₆H₄—N—CH₂—SO—CH₂ (5-membered ring with SO)

I-29

(C₆H₁₃)₂N—C₆H₃(CH₃)—N(CH₂CH₂)₂SO (7-membered ring with SO, methyl substituent)

I-30

CH₃(tetrahydrofuran-2-yl)N—C₆H₄—N(CH₂)₃SO(CH₂)₃ (8-membered ring with SO)

I-31

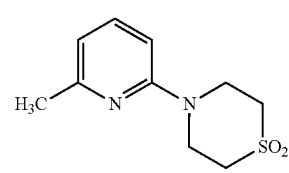

[Chemical formula 11]

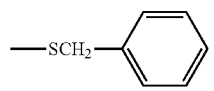

| Compound | R$_2$ | m5 | R$_3$ | | l5 |
|---|---|---|---|---|---|
| I-32 | — | 0 | —SCH$_2$—C$_6$H$_5$ | (7) | 1 |
| I-33 | — | 0 | —OC$_8$H$_{17}$ | (7) | 1 |
| I-34 | — | 0 | —OC$_{13}$H$_{27}$(i) | (7) | 1 |
| I-35 | — | 0 | —OC$_{14}$H$_{29}$ | (7) | 1 |
| I-36 | — | 0 | —OC$_{18}$H$_{37}$ | (7) | 1 |
| I-37 | — | 0 | —OC$_{12}$H$_{25}$ | (5) | 1 |
| I-38 | — | 0 | —NHCO—C$_6$H$_5$ | (7) | 1 |
| I-39 | — | 0 | —OCH$_3$ | (6,8) | 2 |
| I-40 | — | 0 | —N(C$_2$H$_5$)(C$_8$H$_{17}$) | (7) | 1 |
| I-41 | — | 0 | —OC$_{12}$H$_{25}$ (7) —Cl (6) | | 2 |

-continued

[Chemical formula 11]

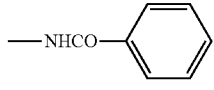

| Compound | R$_2$ | m5 | R$_3$ | | l5 |
|---|---|---|---|---|---|
| I-42 | — | 0 | —O—C(=O)—C$_{13}$H$_{27}$ | (7) | 1 |
| I-43 | — | 0 | —OC$_{12}$H$_{25}$ | (7) | 1 |
| I-44 | — | 0 | —NHCOOC$_{12}$H$_{25}$ | (5) | 1 |
| I-45 | —CH$_3$ | (1,1,4,4) 4 | —OC$_{12}$H$_{25}$ | (7) | 1 |
| I-46 | —CH$_3$ | (2,2,3,3) 4 | —OC$_{16}$H$_{33}$ | (7) | 1 |
| I-47 | — | 0 | —OC$_{12}$H$_{25}$ | (5) | 1 |
| I-48 | — | 0 | —OCH$_2$—C$_6$H$_5$ | (7) | 1 |
| I-49 | — | 0 | —NHSO$_2$C$_{18}$H$_{37}$ | (5) | 1 |
| I-50 | —CH$_2$OH | (1) 1 | —O—C(=O)—C$_{13}$H$_{27}$ | (7) | 1 |
| I-51 | —CH$_3$ | (2,2,3,3) 4 | —OC$_{12}$H$_{25}$ | (7) | 1 |

[Chemical formula 12]

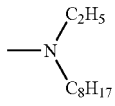

| Compound | R$_2$ | m5 | R$_3$ | | l5 |
|---|---|---|---|---|---|
| I-52 | — | 0 | —OC$_{14}$H$_{29}$ | (6) | 1 |
| I-53 | — | 0 | —OC$_2$H$_5$ | (5,7) | 2 |
| I-54 | — | 0 | —NHSO$_2$—C$_6$H$_4$—OC$_{12}$H$_{25}$ | (7) | 1 |
| I-55 | —OC$_2$H$_5$ | (1) 1 | —OC$_{12}$H$_{25}$ | (5) | 1 |
| I-56 | —CH$_3$ | (3,3) 2 | —OCH$_2$—C$_6$H$_5$ | (7) | 1 |

I-57

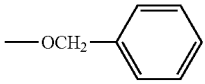

I-58

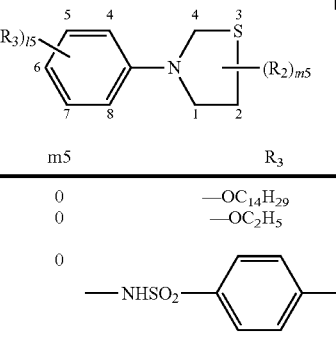

I-59

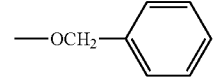

-continued

[Chemical formula 12]

Structure: Phenyl ring with positions 5,4 bearing $(R_3)_{l5}$ at 6, connected at position 8 to N(1), which connects to ring with positions 2,3,4 and S, where position 2 bears $(R_2)_{m5}$.

| Compound | R₂ | m5 | R₃ | l5 |
|---|---|---|---|---|

I-60: R₃ = 4-methyl-N,N-di(C₆H₁₃)amino on ring, with thiazinane-S-oxide (SO)

I-61: R₃ = N-methyl-N-(tetrahydrofuran-2-yl)amino, with 8-membered ring containing SO I-62: 2-methyl-6-(thiomorpholine-1,1-dioxide)pyridine

[Chemical formula 13]

Structure: phenyl ring (positions 5,6,7,8,9 with $(R_3)_{l5}$) — N(1) — ring (2,3,4 and SO) with $(R_2)_{m5}$

| Compound | R₂ | m5 | R₃ | l5 |
|---|---|---|---|---|
| I-63 | — | 0 | —SCH₂—C₆H₅ (7) | 1 |
| I-64 | — | 0 | —OC₈H₁₇ (7) | 1 |
| I-65 | — | 0 | —OC₁₃H₂₇(i) (7) | 1 |
| I-66 | — | 0 | —OC₁₄H₂₉ (7) | 1 |
| I-67 | — | 0 | —OC₁₈H₃₇ (7) | 1 |
| I-68 | — | 0 | —OC₁₂H₂₅ (5) | 1 |
| I-69 | — | 0 | —NHCO—C₆H₅ (7) | 1 |
| I-70 | — | 0 | —OCH₃ (6,8) | 2 |
| I-71 | — | 0 | —N(C₂H₅)(C₈H₁₇) (7) | 1 |
| I-72 | — | 0 | —OC₁₂H₂₅ (7) | —Cl (6) 2 |
| I-73 | — | 0 | —O—C(=O)—C₁₃H₂₇ (7) | 1 |
| I-74 | — | 0 | —OC₁₂H₂₅ (7) | 1 |
| I-75 | — | 0 | —NHCOOC₁₂H₂₅ (5) | 1 |
| I-76 | —CH₃ | (1,1,4,4) 4 | —OC₁₂H₂₅ (7) | 1 |

-continued

[Chemical formula 13]

| Compound | R₂ | m5 | R₃ | l5 |
|---|---|---|---|---|
| I-77 | —CH₃ | (2,2,3,3) 4 | —OC₁₆H₃₃ (7) | 1 |
| I-78 | — | 0 | —OC₁₂H₂₅ (5) | 1 |
| I-79 | — | 0 | —OCH₂—C₆H₅ (7) | 1 |
| I-80 | — | 0 | —NHSO₂C₁₈H₃₇ (5) | 1 |
| I-81 | —CH₂OH | (1) 1 | —O—C(=O)—C₁₃H₂₇ (7) | 1 |
| I-82 | —CH₃ | (2,2,3,3) 4 | —OC₁₂H₂₅ (7) | 1 |

[Chemical formula 14]

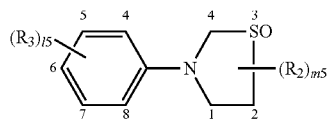

| Compound | R₂ | m5 | R₃ | | l5 |
|---|---|---|---|---|---|
| I-83 | — | 0 | —OC$_{14}$H$_{29}$ | (6) | 1 |
| I-84 | — | 0 | —OC$_2$H$_5$ | (5,7) | 2 |
| I-85 | — | 0 | —NHSO$_2$—C$_6$H$_4$—OC$_{12}$H$_{25}$ | (7) | 1 |
| I-86 | —OC$_2$H$_5$ (1) | 1 | —OC$_{12}$H$_{25}$ | (5) | 1 |
| I-87 | —CH$_3$ (3,3) | 2 | —OCH$_2$—C$_6$H$_5$ | (7) | 1 |
| I-88 | | | C$_{12}$H$_{25}$O—C$_6$H$_4$—N(CH$_2$CH$_2$)$_2$CH$_2$SO$_2$ (7-membered ring) | | |
| I-89 | | | C$_{12}$H$_{25}$O—C$_6$H$_4$—N-ring-SO$_2$ (8-membered ring) | | |
| I-90 | | | C$_{12}$H$_{25}$O—C$_6$H$_4$—N-ring-SO (5-membered) | | |
| I-91 | | | (C$_6$H$_{13}$)$_2$N—C$_6$H$_3$(CH$_3$)—N-ring-SO (7-membered) | | |
| I-92 | | | CH$_3$(tetrahydrofuran-2-yl)N—C$_6$H$_4$—N-ring-SO (8-membered) | | |
| I-93 | | | 6-methylpyridin-2-yl—N-ring-SO$_2$ (thiomorpholine dioxide) | | |

[Chemical formula 15]

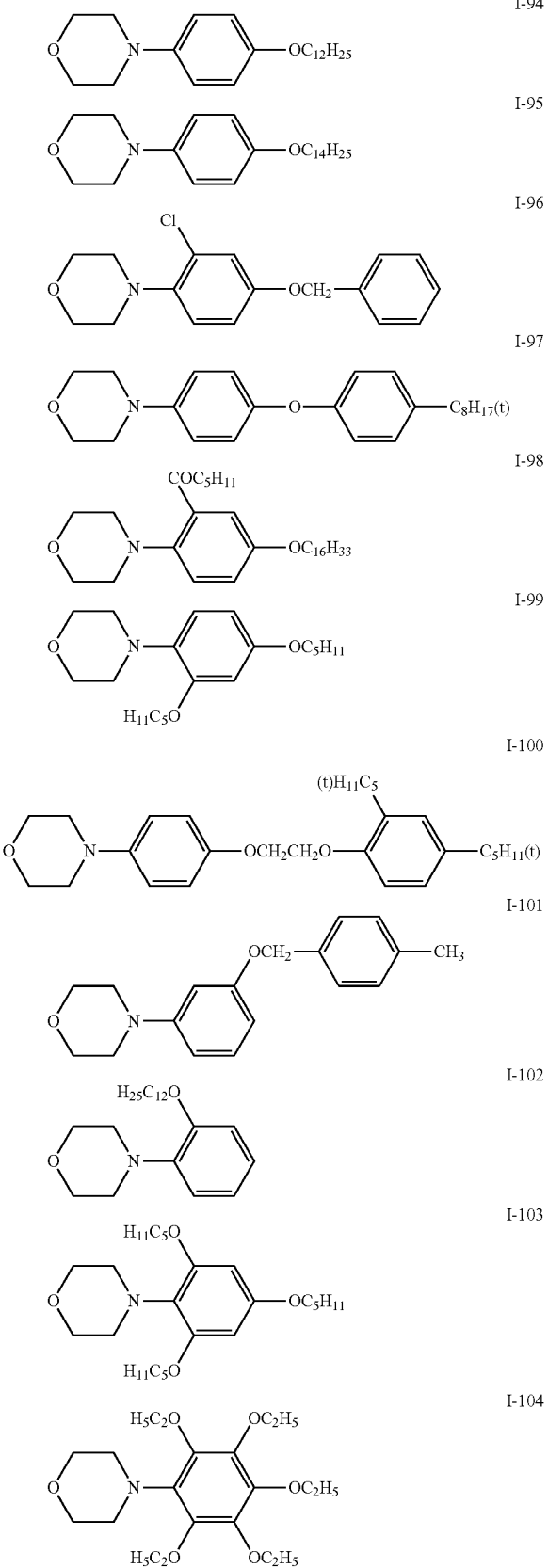

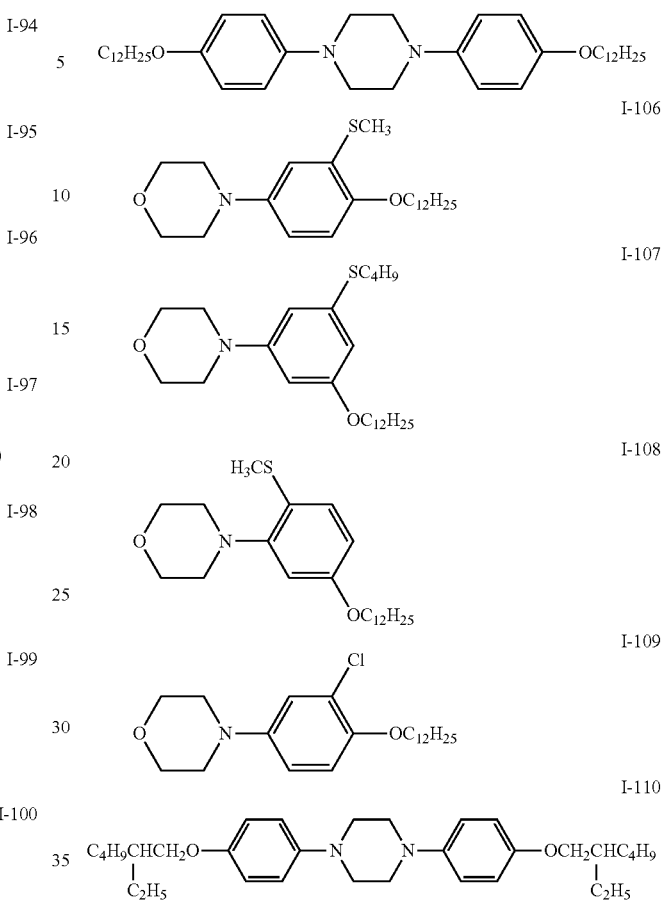

Next, the antioxidant represented by general formula (II) is explained.

In general formula (II), $R_4$ represents a hydrogen atom, a substituted or unsubstituted alkyl group, or a substituted or unsubstituted trialkylsilyl group, and in general formula (II), examples of $R_4$ include a hydrogen atom, an alkyl group having 1 to 20 carbon atoms (such as methyl, ethyl, octyl, and lauryl), and a trialkylsilyl group having 1 to 20 carbon atoms (such as a trimethylsilyl group, a dimethylpropylsilyl group, and a triethylsilyl group).

In general formula (II), $R_5$, $R_6$, $R_7$, $R_8$ and $R_9$ each represents a hydrogen atom, a substituted or unsubstituted alkyl group, a substituted or unsubstituted alkoxy group, an aryl group, a substituted or unsubstituted aryloxy group, a substituted or unsubstituted alkenyl group, a substituted or unsubstituted alkenyloxy group, a substituted or unsubstituted acylamino group, a halogen atom, a substituted or unsubstituted alkylthio group, a substituted or unsubstituted arylthio group, a substituted or unsubstituted alkoxycarbonyl group, a substituted or unsubstituted acyloxy group, a substituted or unsubstituted acyl group, a substituted or unsubstituted sulfonamide group, a substituted or unsubstituted trialkylsilyl group, a substituted or unsubstituted heterocyclic ring, a substituted or unsubstituted fused ring, or a combination thereof. Meanwhile, the expression "substituted or unsubstituted" means that all of the aforementioned substituent groups may be substituted.

In general formula (II), examples of each of $R_5$, $R_6$, $R_7$, $R_8$ and $R_9$ include a hydrogen atom, an alkyl group having 1 to 20 carbon atoms (such as methyl, ethyl, octyl, and lauryl), an alkoxy group having 1 to 20 carbon atoms (such as methoxy, ethoxy, butyloxy, and octyloxy), an aryl group (such as phenyl and naphthyl), an aryloxy group having 6 to 20 carbon atoms (such as phenoxy and naphthoxy), an alkenyl group having 2 to 20 carbon atoms (such as octenyl), an alkenyloxy group having 2 to 20 carbon atoms (such as octenyloxy), an acylamino group having 2 to 20 carbon atoms (such as acetylamino, palmitoylamino, and benzoylamino), a halogen atom (such as chlorine and bromine), an alkylthio group having 1 to 20 carbon atoms (such as octylthio and laurylthio), an arylthio group having 6 to 20 carbon atoms (for example, phenylthio), an alkoxycarbonyl group having 1 to 20 carbon atoms group (such as methoxycarbonyl, ethoxycarbonyl, and hexadecyloxycarbonyl), an acyloxy group having 2 to 20 carbon atoms (such as acetyloxy and benzoyloxy), an acyl group having 2 to 20 carbon atoms (such as acetyl, valeryl, stearoyl, and benzoyl), a sulfonamide group having 1 to 20 carbon atoms (such as octylsulfonamide and lauryl sulfonamide), a trialkylsilyl group having 1 to 20 carbon atoms (such as a trimethylsilyl group, a dimethylpropylsilyl group, and a triethylsilyl group), a heterocyclic ring containing O (such as oxolane (tetrahydrofuran) and oxane (tetrahydropyran)), and a fused ring (a fused ring of heterocyclic ring and benzene (such as chromane)). Further, those groups may have a spiro atom which additionally forms a ring by sharing a carbon with other ring. Examples of the ring contained in the spiro atom include tetrahydropyran and chromane. Further, those substituent groups may be further substituted with an alkyl group or alkoxy group having 1 to 20 carbon atoms or an aryl group having 6 to 20 carbon atoms.

Further, two groups from $R_4$ to $R_9$ may be linked to each other to form a substituted or unsubstituted 5- to 6-membered ring (such as indane, spiroindane, chromane, and spirochromane ring). Specifically, it is in the form in which two groups of from $R_4$ to $R_9$ are linked to each other to form a heterocyclic ring such as oxolane (tetrahydrofuran) and oxane (tetrahydropyran) and fused with a phenyl ring represented by general formula (II). Further, the 5- to 6-membered ring (heterocyclic ring) may additionally have a substituent group, and examples of the substituent group include an alkyl group or alkoxy group having 1 to 20 carbon atoms and an aryl group having 6 to 20 carbon atoms, or they may additionally form a ring. Further, the concept of the substituent group contained in the 5- to 6-membered ring (heterocyclic ring) also includes other ring in which a carbon constituting the 5- to 6-membered ring (heterocyclic ring) is shared with another ring to form additionally a ring. Examples of the substituent group for a case in which the 5- to 6-membered ring (heterocyclic ring) has a spiro atom include teterahydropyran, chromane or the like. Meanwhile, any carbon among those substituent groups is shared with the 5- to 6-membered ring (heterocyclic ring). Preferred mode of the above forms is represented by general formula (II-1), general formula (II-2), or general formula (II-3).

[Chemical formula 16]

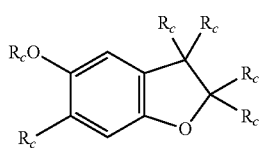

(II-1)

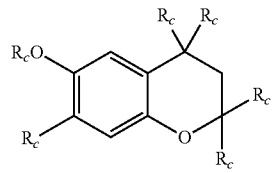

(II-2)

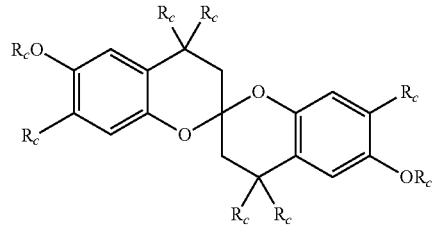

(II-3)

In general formulas (II-1) to (II-3), $R_c$ represents a hydrogen atom or an alkyl group or an alkoxy group having 1 to 20 carbon atoms. As for the alkyl group or alkoxy group having 1 to 20 carbon atoms, the same substituent groups as the substituent groups for the aryl group represented by $R_1$ can be employed.

In general formula (II), $R_6$ and $R_8$ are preferably not an alkoxy group.

In general formula (II), those represented by the above general formula (II-A) are preferable.

In general formula (II-A), $R_{10}$ to $R_{13}$ each independently represents a hydrogen atom or a substituted or unsubstituted alkyl group. Wherein, $R_{11}$ and $R_{13}$ may be linked to each other to form a substituted or unsubstituted 5- to 6-membered ring. A mode in which $R_{11}$ and $R_{13}$ are linked to each other to form a 5- to 6-membered ring is the same as the mode in which two groups of $R_4$ to $R_9$ are linked to each other to form a substituted or unsubstituted 5- to 6-membered ring. In other words, it is also the same as above in that the concept of the substituent group contained in the 5- to 6-membered ring also includes other ring in which a carbon constituting the 5- to 6-membered ring is a spiro atom shared with another ring to form additionally a ring. Examples of the substituent group for a case in which the 5- to 6-membered ring has a spiro atom include teterahydropyran, chromane or the like, similarly. Examples of the preferred mode for a case in which $R_{11}$ and $R_{13}$ are linked to each other include the mode of general formulas (II-1) to (II-3) in general formula (II).

In general formula (II-A), it is preferable that $R_{10}$ to $R_{13}$ each independently represents an alkyl group, or it is a mode of general formula (II-1), general formula (II-2) and general formula (II-3) in which $R_{10}$ represents an alkyl group and $R_{11}$ and $R_{13}$ are linked to each other to form 5- to 6-membered ring.

Examples of $R_{10}$ to $R_{13}$ include an alkyl group having 1 to 20 carbon atoms (such as methyl, ethyl, octyl, and lauryl).

Hereinbelow, specific examples of a compound represented by general formula (II) are given, but the present invention is not limited to them.

[Chemical formula 17]
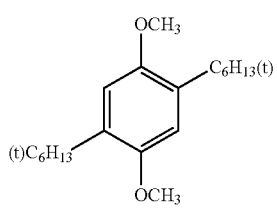 II-1
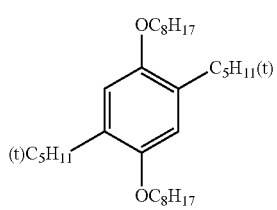 II-2
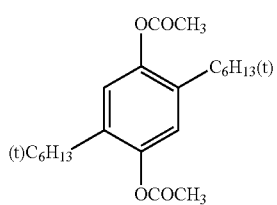 II-3
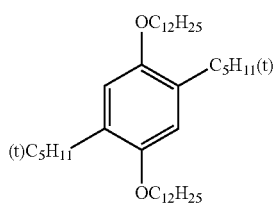 II-4
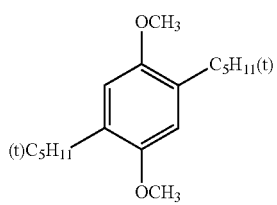 II-5
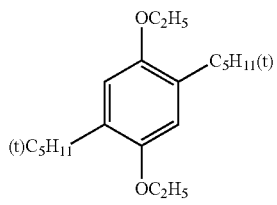 II-6
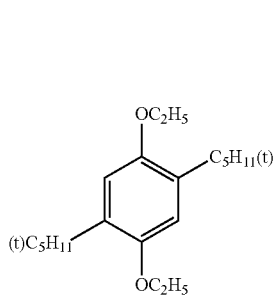 II-7
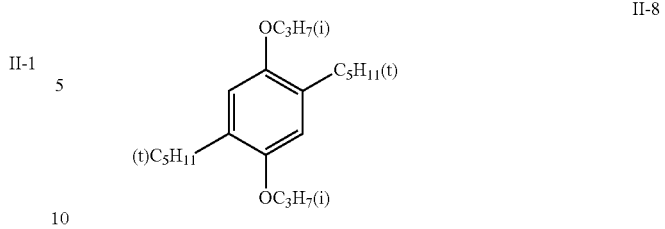 II-8
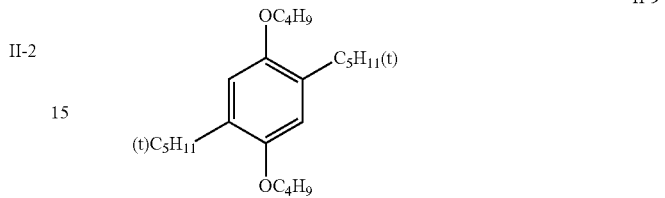 II-9
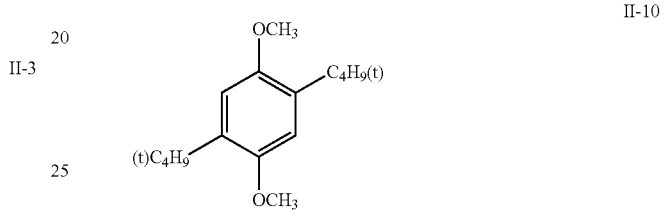 II-10
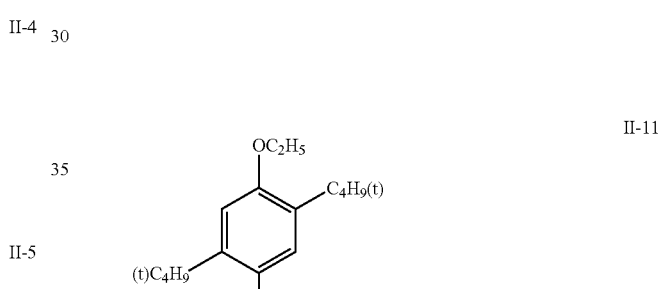 II-11
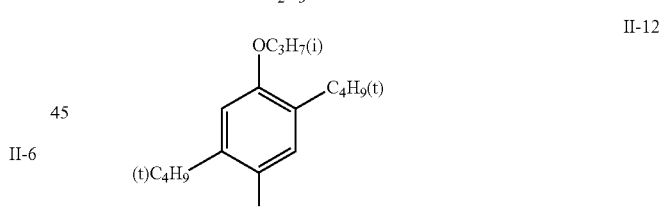 II-12
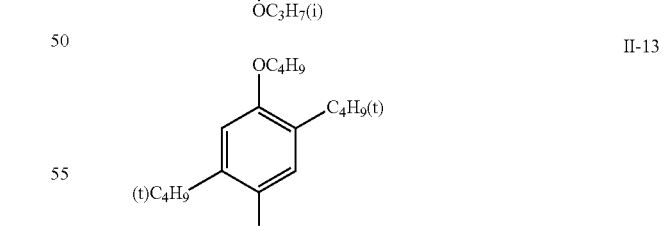 II-13
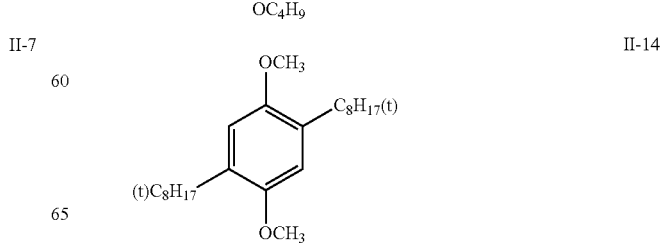 II-14

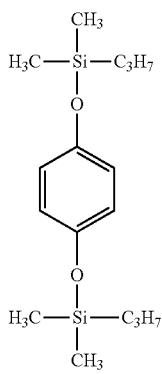

[Chemical formula 18]

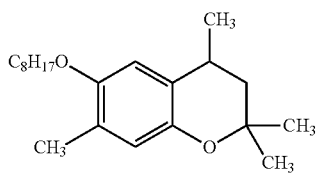

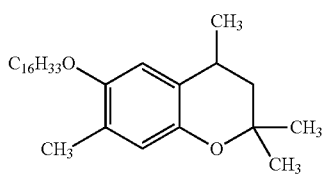

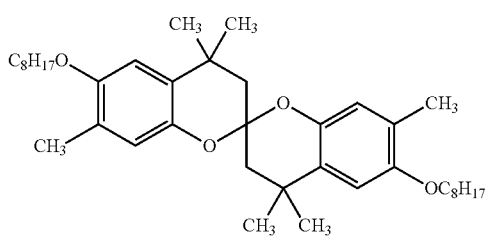

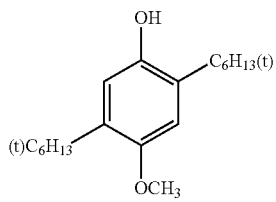

[Chemical formula 19]

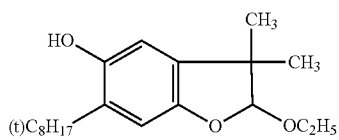

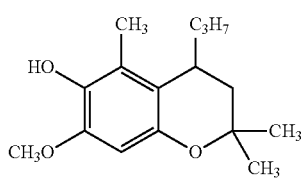

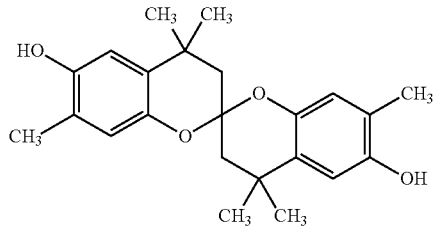

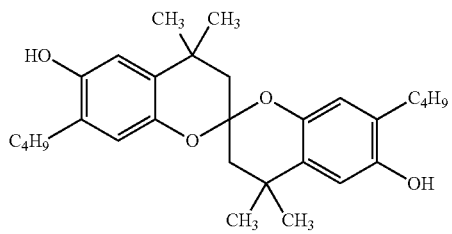

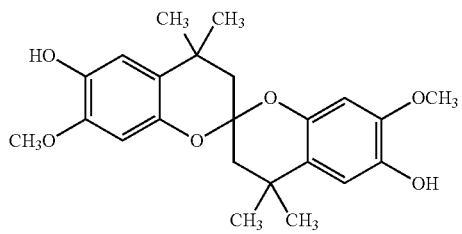

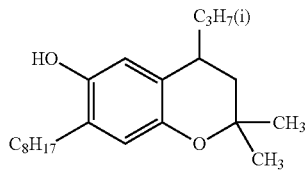

In the present invention, by including the antioxidant with the above structure in a power generation layer, it exhibits a function as an oxygen scavenger for quenching singlet oxygen, and as a result, excellent durability is obtained when irradiated with light. Although the mechanism remains unclear, it is presumed that, according to the structure of cyclic tertiary amine in general formula (I) and the cyclic ether structure of general formula (II) of the antioxidant, energy transfer from singlet oxygen occurs efficiently and energy is consumed by the antioxidant according to fluorescence emission or thermal non-radiative deactivation. However, the present invention is not limited to that mechanism.

In the present invention, each antioxidant explained above is preferably added in a range of 0.1 to 15 parts by mass with respect to 100 parts by mass of an organic semiconductor material. When the addition amount of the antioxidant is 0.1 parts by mass or more, photodegradation can be suppressed in the present invention. On the other hand, when the addition amount of the antioxidant is 15 parts by mass or less, inhibited power generation can be suppressed. Meanwhile, the addition amount of the antioxidant is more preferably 0.5 to 12 parts by mass, and particularly preferably 0.7 to 10 parts by mass with respect to 100 parts by mass of an organic semiconductor material. Meanwhile, said organic semiconductor material means sum of the p-type semiconductor and n-type semiconductor used for the power generation layer.

As described above, by adding the antioxidant according to the present invention, attenuation of short circuit current (Jsc) can be suppressed even when the photoelectric conversion element is placed under light irradiation, and thus device lifetime of the solar cell can be extended.

<Solubility Parameter>

The antioxidant which can be preferably used in the present invention preferably has solubility parameter (SP value) ranging from 19 to 23. Meanwhile, in the present application, the "solubility parameter value (SP value)" indicates criteria of mutual solubility of at least two components that is based on the theory established by Hansen. The parameter value itself is represented as an indicator of intermolecular force. Thus, examples of those having high SP value include a polar compound such as water and those having low SP value include a hydrophobic compound.

The solubility parameter can be calculated using the method explained in Hansen Solubility Parameters A, User's Handbook, 2nd Ed (CRC Press).

Further, it is also possible that the solubility parameter of an organic compound is deduced from its molecular structure. It can be calculated using a simulation software that calculates the solubility parameter based on SMILE equation, for example, HSPiP (http://www.hansen-solubility-.com). The solubility parameter used in the present invention is so-called Hansen's solubility parameter which is divided into a dispersion component $\delta D$, a polarization component $\delta P$, and a hydrogen-bonding component $\delta H$, and the solubility parameter can be calculated using the following Mathematical formula (1). Meanwhile, those solubility parameters are obtained based on the theory described in HANSEN SOLUBILITY PARAMETERS, A User's Handbook Second Edition, Charles M. Hansen.

Mathematical formula(1)solubility parameter=
$$\sqrt{\delta D^2 + \delta P^2 + \delta H^2}$$ [Mathematical 1]

Solubility parameter (SP value) of the antioxidant which may be preferably used in the present invention preferably is preferably in a range of 16 to 28, more preferably in a range of 17 to 25, even more preferably in a range of 19 to 23. In particular, it ranges preferably from 19.5 to 22.5, and more preferably 20 to 22.

When the solubility parameter is 16 or higher, it is soluble in a p-type organic semiconductor and an n-type organic semiconductor, and when it is 28 or lower, it is at least soluble in an n-type organic semiconductor, and therefore desirable. Meanwhile, using the p-type organic semiconductor and n-type organic semiconductor with solubility parameter of preferably 16 to 28, more preferably 17 to 25, and even more preferably 18 to 22, the effects are exhibited more. Specifically, the difference in solubility parameter between a p-type organic semiconductor and/or an n-type organic semiconductor and an antioxidant is preferably 5 or less, more preferably 3 or less, and even more preferably 2 or less.

By selecting an antioxidant added to a p-type organic semiconductor material and an n-type organic semiconductor material having solubility parameter within the preferred range described above, the antioxidant can be added without significantly inhibiting the power generation efficiency. In the preferred range of the present invention, in particular, it is believed that the crystalline property of a p-type organic semiconductor material is not inhibited due to an effect of being more soluble at an n-type organic semiconductor material side, and thus the addition can be effectively made without affecting the power generation efficiency. Although the mechanism remains unclear, it is believed that the solubility parameter of the antioxidant is present in a domain of an organic semiconductor having closer solubility parameter, and accordingly, the inhibited conversion efficiency is suppressed even when an antioxidant is added. In the present invention, it is more preferable that the antioxidant is present in a domain at an n-type organic semiconductor material side, and thus the effect of not inhibiting the conversion efficiency is exhibited more. In other words, it is particularly preferable that the difference in solubility parameter between an antioxidant and an n-type organic semiconductor is in the aforementioned range. Meanwhile, the presented invention is not limited to that mechanism.

<p-Type Organic Semiconductor Material>

Examples of the p-type organic semiconductor material used for the power generation layer (bulk heterojunction layer) of the present invention include various fused polycyclic aromatic compounds with low molecular weight or conjugated polymers.

Examples of the fused polycyclic aromatic compound with low molecular weight include a compound such as anthracene, tetracene, pentacene, hexacene, heptacene, chrysene, picene, fulminene, pyrene, peropyrene, perylene, terylene, quoterylene, coronene, ovalene, circumanthracene, bisanthene, zethrene, heptazethrene, pyanthrene, violanthene, isoviolanthene, circobiphenyl, or anthradithiophene, porphyrin, copper phthalocyanine, tetrathiafulvalene (TTF)-tetracyanoquinodimethane (TCNQ) complex, bisethylene tetrathiafulvalene (BEDTTTF)-perchloric acid complex, and a derivative or a precursor thereof.

Examples of the derivative having fused polycycle include pentacene derivatives with a substituent group that are described in WO 03/16599 A, WO 03/28125 A, the specification of U.S. Pat. No. 6,690,029, and JP 2004-107216 A, pentacene precursors disclosed in the detailed description of US 2003/136964 or the like, and acene-based compounds substituted with tialkylsilyl ethynyl group described in J. Amer. Chem. Soc., vol. 127. No. 14, 4986, J. Amer. Chem. Soc., vol. 123, p 9482, J. Amer. Chem. Soc., vol. 130 (2008), No. 9, 2706, or the like.

Examples of the conjugated polymers include polythiophene and its oligomer such as poly 3-hexylthiophene (P3HT), polythiophene having a polymerizable group described in Technical Digest of the International PVSEC-17, Fukuoka, Japan, 2007, p 1225, a polythiophene-thienothiophene copolymer described in Nature Material, (2006) vol. 5, p 328, a polythiophene-diketopyrrolopyrrole copolymer described in WO2008000664, a polythiophene-thiazolothiazole copolymer described in Adv. Mater., 2007 p 4160, PFDTBT described in APPLIED PHYSICS LETTERS vol. 92, p 033307 (2008), and PTB1 to 6 described in J. Amer. Chem. Soc., vol. 131, p 7792 (2009). Among them, in the present invention, a polythiophene copolymer such as the polythiophene-carbazole-benzothiazole copolymer (PCDTBT) described in Adv. Mater., vol. 19 (2007) p 2295, which is a low-band gap polymer having absorption for a wavelength longer than 650 nm or PCPDTBT described in Nature Mat. vol. 6 (2007), p 497 are preferable.

<n-Type Organic Semiconductor Material>

The n-type organic semiconductor material used for the bulk heterojunction layer of the present invention is not particularly limited, but the examples thereof include fullerene, octaazaporphyrin, a perfluoro compound of a p-type semiconductor (perfluoropentacene and perfluorophthalocyanine), and a polymer compound containing carboxylic anhydride or its imide compound as a backbone such as naphthalene tetracarboxylic anhydride, naphthalene tetracarboxylic diimide, perylene tetracarboxylic anhydride, or perylene tetracarboxylic diimide.

When the material having a thiophene-containing fused ring of the present invention is used as a p-type organic semiconductor material, a fullerene derivative capable of performing efficient charge separation is preferable. Examples of the fullerene derivative include fullerene C60, fullerene C70, fullerene C76, fullerene C78, fullerene C84, fullerene C240, fullerene C540, mixed fullerene, fullerene nano tube, multi layer nano tube, mono layer nano tube, and nano horn (cone type) or the like, and a fullerene derivative partially substituted with a hydrogen atom, a halogen atom, a substituted or unsubstituted alkyl group, an alkenyl group, an alkynyl group, an aryl group, a heteroaryl group, a cycloalkyl group, a silyl group, an ether group, a thioether group, an amino group, or a silyl group and the like.

Among them, a fullerene derivative having a substituent group and more improved solubility such as [6,6]-phenyl C61-butyric acid methyl ester (abbreviation: PCBM ($PC_{60}BM$)), [6,6]-phenyl C61-butyric acid-n butyl ester (PCBnB), [6,6]-phenyl C61-butyric acid-isobutyl ester (PCBiB), [6,6]-phenyl C61-butyric acid-n-hexyl ester (PCBH), bis-PCBM described in Adv. Mater., vol. 20 (2008), p 2116 or the like, an amino-fullerene described in JP 2006-199674 A, a metalocenized fullerene described in JP 2008-130889 A, or a fullerene having a cyclic ether group described in U.S. Pat. No. 7,329,709 is preferably used.

<Electrode>

The organic photoelectric conversion element according to the present invention includes at least a transparent first electrode (hereinbelow, also referred to a transparent electrode) and a second electrode (herein below, also referred to as a counter electrode). Further, in case of having a tandem configuration, by using an intermediate electrode, it is possible to achieve the tandem configuration. Hereinbelow, a preferred configuration of the transparent electrode and counter electrode is described.

Meanwhile, the transparent electrode and counter electrode are the names of an electrode that are determined from function like presence or absence of light transmitting property. When classification of electrodes is made based on flowing type of carrier, the electrode through which mainly holes flow are referred to as an anode and the electrode through which mainly electrons flow are referred to as a cathode in the present invention.

When the first electrode is an anode, since it is a configuration in which holes are mainly extracted from the carriers consisting of holes and electrons, it is preferable to include a hole transport layer between the first electrode and the power generation layer. Similarly, when the second electrode is a cathode, since it is a configuration in which electrons are mainly extracted, it is preferable to include an electron transport layer between the second electrode and the power generation layer <Transparent Electrode>

As a transparent electrode of the organic photoelectric conversion element, those having a metal, an alloy, an electroconductive compound, and a mixture thereof as an electrode material are preferably used. As described herein, the term "transparent" means that transmittance of at least 80% is exhibited for visible light with wavelength of 550 nm.

The material composition with optimum work function can be selected depending on configuration of adhesion to a charge transport layer. Examples of the composition with small work function include an ultra-thin film of sodium, sodium-potassium alloy, magnesium, lithium, magnesium/copper mixture, magnesium/silver mixture, magnesium/aluminum mixture, magnesium/indium mixture, aluminum/aluminum oxide ($Al_2O_3$) mixture, indium, lithium/aluminum mixture, or rare earth metal and the like. Further, examples of the composition with large work function include an ultra-thin film of gold, silver, or platinum, nano particles•nano wire layers of them, a conductive metal oxide material such as indium tin oxide (ITO), $SnO_2$, or ZnO, and a conductive polymer or the like. Further, it is also possible to use an amorphous material such as IDIXO ($In_2O_3$—ZnO) which can be prepared into a light-transmitting conductive film.

Further, having a transparent electrode with both high transmittance and high conductivity by using the metal thin film, nano particles•nano wires, and conductive metal oxide materials in combination is also a preferred mode of the present invention.

Further, according to the present invention, not to decrease significantly the fill factor even when a large area is to be obtained, it is preferable that an auxiliary electrode including an opening is used in combination (also referred to as a grid electrode or a bus line electrode).

The auxiliary electrode is preferably a metal from the viewpoint of having good conductivity. Examples of the metallic material include gold, silver, copper, iron, nickel, and chrome or the like. Further, the metal in conduction part may be an alloy, and the metal layer may be either a monolayer or a multilayer.

Shape of the auxiliary electrode is not particularly limited, but for example, the conduction part has a stripe shape, a mesh shape, or a random fishnet shape. The method for forming an auxiliary electrode in which the conduction part has a stripe shape, a mesh shape, or a random fishnet shape is not particularly limited, and a conventionally well-known method can be used. For example, it may be formed by a well-known photolithography method after forming a metal layer over entire surface of a substrate. Specifically, after forming a conductor layer using one or two or more physical or chemical forming method such as vapor deposition, sputtering, or plating on entire surface of a substrate or laminating a metal foil on a substrate using adhesives, processing into a desired stripe shape or a mesh shape can be achieved by etching using a well-known photolithography method.

Examples of other method which may be used include a printing an ink containing metal microparticles to have a desired shape using various printing methods such as screen printing, flexo printing, gravure printing, or inkjet method, a method of performing plating after coating platable catalyst ink to have a desired shape by the aforementioned various printing methods, or a method of applying silver halide photographic technique. Among those methods, the method of printing an ink containing metal microparticles to have a desired shape using various printing methods allows production with simple processes, and thus incorporation of impurities which cause leakage during production can be reduced and also liquid loss is small as the ink is used only for a necessary area and there is no problem of contamination by incompletely removed chemicals as no special chemical treatment are required, and thus it corresponds to the most preferred embodiment of the present invention.

Sheet resistance of the transparent electrode is preferably several hundred $\Omega/\square$ or less, more preferably $50\Omega/\square$ or less, and even more preferably $15\Omega/\square$ or less. Further, although it may vary depending on materials, the film thickness is generally selected from the range of 10 to 1000 nm, and preferably from the range of 100 to 200 nm, from the viewpoint of transmittance/resistance.

Further, when an auxiliary electrode is present, it is preferably 10Ω/□ or less, and more preferably 0.01 to 8Ω/□. In such case, the sheet resistance is determined by the shape of auxiliary electrode (line width, height, pitch, and shape), and for a material having higher resistance than an auxiliary electrode, it is hardly affected by the resistance of a window part.

<Counter Electrode>

Meanwhile, as a counter electrode, those containing a metal, an alloy, an electroconductive compound, and a mixture thereof as an electrode material are also preferably used. However, the metal is not required to be a thin film and, when desired electric conductivity is obtained, the film thickness or composition is not particularly limited. Further, a material with optimum work function is preferably selected depending on an adjacent charge transport layer. Specific materials which may be used are the same as those exemplified above for the transparent electrode.

In case of a configuration in which electrons are extracted from a counter electrode side, by selecting a material with even smaller work function among the aforementioned materials, the electrons can be efficiently extracted, and therefore desirable.

<Charge Transport Layer: Hole Transport Layer, Electron Transport Layer>

The charge transport layer has, as an intrinsic function, a role of blocking layer for transporting only the holes or electrons generated in the power generation layer to an electrode and blocking transport of opposite carriers. In other words, the hole transport layer can be referred to as an electron blocking layer and the electron transport layer can be referred to as a hole blocking layer for such case.

In broad sense, the hole blocking layer has a function of an electron transport layer, and more particularly, it consists of a hole blocking material which has a function of transporting electrons and a significantly low ability of transporting holes, and by blocking holes while transporting electrons, the recombination ratio between electrons and holes on the electrode can be enhanced. Further, the configuration of the electron transparent layer described below can be employed for the hole blocking layer according to the present invention, if necessary. The hole blocking layer is preferably formed adjacent to the power generation layer.

Meanwhile, in broad sense, the electron blocking layer has a function of an hole transport layer, and more particularly, it consists of a material which has a function of transporting holes and a significantly low ability of transporting electrons, and by blocking electrons while transporting holes, the recombination ratio between electrons and holes can be enhanced. Further, the configuration of the hole transport layer described below can be employed for the electron blocking layer, if necessary.

As described above, the dry film thickness of the charge transport layer of the present invention is preferably 5 to 2000 nm. In particular, the charge transport layer at the side for forming an electrode at later stage (for example, 18 in FIG. 1) preferably has film thickness of 50 nm or more from the viewpoint of suppressing damage at the time of forming an electrode. From the viewpoint of increasing the effect of preventing leakage, the film thickness is more preferably 100 nm or more. Further, from the viewpoint of maintaining high transmittance and reduced resistance as a film, the film thickness is more preferably 1000 nm or less.

Meanwhile, the charge transport layer on the substrate side (for example, 12 in FIG. 1) preferably has film thickness of 200 nm or less. From the viewpoint or film resistance and light transmittance, it is more preferably 3 to 100 nm, and most preferably 5 to 100 nm.

<Hole Transport Layer>

The hole transport layer contains a hole transport material having a function of transporting holes, and in broad sense, it also includes a hole injection layer and an electron blocking layer. The hole transport layer may be formed as a monolayer or a multilayer.

The hole transport material has any one of hole injection or transport property, or an electron blocking property, and it may be any one of an organic material and an inorganic material. Examples thereof include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styryl anthracene derivative, a fluorenone derivative, a hydrazone derivative, a stilbene derivative, a silazane derivative, an aniline-based copolymer, or a conductive polymer oligomer, in particular a thiophene oligomer such as poly(3,4-ethylenedioxythiophene) (PEDOT), a styrene oligomer such as poly(4-styrene sulfonic acid) (PSS), and a mixture thereof.

As a hole transport material, those described above can be used, but a porphyrin compound, an aromatic tertiary amine compound, or a styrylamine compound, in particular, an aromatic tertiary amine compound is preferably used.

Further, a polymer material can be also used, in which those materials are introduced to the polymer chain or having those materials as a main chain of the polymer. Further, inorganic compounds such as p-type-Si, p-type-SiC, nickel oxide, or molybdenum oxide can be also used as a hole injection material or a hole transport material.

Further, so-called p-type hole transport materials described in various applications including JP Hei-11-251067 A, J. Huang et. al. (Applied Physics Letters 80 (2002), p. 139) or the like can be also used.

Further, a hole transport layer doped with impurities to have high p-property can be also used. Examples thereof include those described in JP Hei-4-297076 A, JP 2000-196140 A, JP 2001-102175 A, or J. Appl. Phys., 95, 5773 (2004) and the like.

<Electron Transport Layer>

The electron transport layer contains a material having a function of transporting electrons, and in broad sense, it also includes an electron injection layer and a hole blocking layer. The electron transport layer may be formed as a monolayer or a multilayer.

As for the material, any material can be selected from well-known compounds and used. Examples thereof include a nitro-substituted fluorene derivative, a diphenyl quinone derivative, a thiopyran oxide derivative, carbodiimide, a fluorenylidene methane derivative, an anthraquinodimethane and anthrone derivative, and an oxadiazole derivative or the like. Further, a thiadiazole derivative in which the oxygen atom of oxadiazole ring in the oxadiazole derivative is substituted with a sulfur atom, and a qunoxaline derivative having a quinoxaline ring known as an electron withdrawing group can be also used as an electron transport material. Further, a polymer material can be also used, in which those materials are introduced to the polymer chain or having those materials as a main chain of the polymer.

Further, a metal complex of 8-quinolinol derivative, such as, tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8- quinolinol)aluminum, bis(8-quinolinol) zinc (Znq) or the like, and a metal complex in which the center metal of the metal complex is substituted with In, Mg, Cu, Ca, Sn, Ga, or Pb can be also used as an electron transport material. Other than those, a metal-free or metal phthalocyanine, or those having their terminal substituted with an alkyl group or a sulfonic acid group and the like can be also preferably used as an electron transport material. Similar to the hole injection layer and the hole transport layer, an inorganic semiconductor such as an n-type-Si or n-type-SiC can be also used as an electron transport material.

Further, an electron transport layer doped with impurities to have high n-property can be also used. Examples thereof include those described in JP Hei-4-297076 A, JP Hei-10-270172 A, JP 2000-196140 A, JP 2001-102175 A, J. Appl. Phys., 95, 5773 (2004), or the like.

Further, an inorganic oxide having n-type conductivity (titan oxide, zinc oxide, or the like) can be also used.

Specific examples thereof which may be used include an aromatic diamine compound such as N,N'-bis(3-methylphenyl)-(1,1'-biphenyl)-4,4'-diamine (TPD) or 4,4'-bis[N-(naphthyl)-N-phenyl-amino]biphenyl ($\alpha$-NPD), or a derivative thereof, oxazole, oxadiazole, triazole, imidazole, imidazolone, a stilbene derivative, a pyrazoline derivative, tetrahydroimidazole, polyarylalkane, butadiene, an imine-based compound such as polyethyleneimine, a glycidyl ether-based compound such as glycerol propoxylate triglycidyl ether, a porphyrin compound such as 4,4',4''-tris(N-(3-methylphenyl)N-phenylamino)triphenylamine (m-MTDATA), porphine, copper tetraphenylporphine, phthalocyanine, copper phthalocyanine, and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an anylamine derivative, an amino-substituted chalcone, derivative, an oxazole derivative, a styryl anthracene derivative, a fluorenone derivative, a hydrazone derivative, or a silazane derivative, and as a polymer compound, a polymer of phenylene vinylene, fluorene, carbazole, indole, pyrene, pyrrole, picoline, thiophene, acetylene, or diacetylene, or a derivative thereof can be preferably used.

[Intermediate Electrode]

Further, the material of an intermediate electrode which is required for a tandem configuration is preferably a layer in which a compound having both transparency and conductivity is used. The material used for the aforementioned transparent electrode can be used (transparent metal oxide such as ITO, AZO, FTO, or titanium oxide, very thin metal layer of Ag, Al, or Au, and the like, a layer containing nano particles•nano wires, a conductive polymer material such as PEDOT:PSS, or polyaniline).

Meanwhile, regarding the aforementioned hole transport layer and electron transport layer, there is also a combination in which they work as an intermediate electrode (i.e., charge recombination layer) by lamination after suitable combination, and thus by having such configuration, a process of forming one layer can be omitted, and therefore desirable.

(Transparent Substrate)

The transparent substrate in the present invention indicates a transparent member capable of transmitting light to be photoconverted, i.e., a member transparent against the wavelength of light to be photoconverted. As described herein, "transparent" means that it exhibits transmittance of 80% or higher against the visible light with a wavelength of 550 nm.

Preferred examples of the transparent substrate include such as a glass substrate and a resin substrate. However, from the viewpoint of light-weightness and flexibility, it is preferable to use a transparent resin film. The transparent resin film which may be preferably used as a transparent substrate in the present invention is not particularly limited, and the material, shape, structure, and thickness or the like thereof can be suitably selected from the well-known ones. Examples thereof include a polyester resin film such as polyethylene terephthalate (PET) and polyethylene naphthalate (PEN) modified polyester; a polyolefin resin film such as a polyethylene (PE) resin film, a polypropylene (PP) resin film, a polystyrene resin film, or a cyclic olefin resin; a vinyl resin film such as polyvinyl chloride and polyvinylidene chloride; a polyether ether ketone (PEEK) resin film, a polysulfone (PSF) resin film, a polyether sulfone (PES) resin film, a polycarbonate (PC) resin film, a polyamide resin film, a polyimide resin film, an acrylic resin film and a triacetyl cellulose (TAC) resin film. If the resin film exhibits transmittance for the wavelength of a visible range (380 to 800 nm) of 80% or more, it is preferably applicable to the transparent resin film according to the present invention. Among them, from the viewpoint of transparency, heat resistance, ease of handling, strength and cost, the following resins are preferable: a biaxially stretched polyethylene terephthalate film, a biaxially stretched polyethylene naphthalate film, a polyether sulfone film and a polycarbonate film. Among them, a biaxially stretched polyethylene terephthalate film and a biaxially stretched polyethylene naphthalate film are more preferable.

In order to secure the wettability and the adhesion property of a coating solution, surface treatment can be performed or an easily adhesive layer can be prepared to the transparent substrate used for the present invention. Regarding the surface treatment or an easily adhesive layer, a conventionally well-known technique can be used. For example, as surface treatment, examples thereof include a surface activation process such as corona discharge treatment, flame treatment, ultraviolet treatment, high-frequency treatment, glow discharge process, active plasma treatment, or laser process. Moreover, examples of the easily adhesive layer include such as polyester, polyamide, polyurethane, vinyl-based copolymer, butadiene-based copolymer, acrylic copolymer, vinylidene-based copolymer and epoxy-based copolymer.

Further, for the purpose of suppressing penetration of oxygen and water vapor, a barrier coat layer may be formed in advance on the transparent substrate, and a hard coat layer may be formed in advance on the opposite side to which a transparent conductive layer is transferred.

(Optical Functional Layer)

The organic photoelectric conversion element of the present invention may have, for the purpose of more efficient receiving of sun light, various optical functional layers. As for the optical functional layer, an anti-reflection film, a light collecting layer such as microlens array, or a light diffusing layer for the light reflected from a cathode to enter again the power generation layer may be formed, for example.

As an anti-reflection layer, various well-known anti-reflection layers can be formed. For example, when a transparent resin film is a biaxially stretched polyethylene terephthalate film, by having the refractive index of 1.57 to 1.63 for an easily adhesive layer adjacent to the film, the transmittance can be improved as the interface reflection between the film substrate and easily adhesive layer is lowered, and therefore more desirable. As a method for adjusting the refractive index, it can be performed by suitably adjusting the ratio between oxide sol having relatively high refractive index such as tin oxide sol or cerium oxide sol and a binder resin and coating with it. The easily adhesive layer may be a monolayer. However, to improve the adhesion property, it is possible to have a configuration with two or more layers.

With regard to the light collecting layer, it is possible to increase the light receiving amount in a specific direction by processing to form a structure with microlens array shape at a light receiving side of a supporting substrate or by combining with a so-called light collecting sheet, or on the contrary, the incident angle dependency of sun light can be lowered.

As an example of the microlens array, a quadrangular pyramid having a side length of 30 μm and a vertical angle of 90 degrees is arranged two-dimensionally at a light extraction side of the substrate. It is preferable that a single side has a length of 10 to 100 μm. When it is shorter than that, coloration is caused due to an occurrence of a diffraction effect. On the other hand, when it is excessively long, thickness becomes large, and it is not desirable.

Further, examples of the light scattering layer include various anti-glare layers and a layer in which nano particles•nano wire or the like of metal or various inorganic oxides are dispersed in a colorless and transparent polymer.

(Film Formation Method •Surface Treatment Method)

As for the method of forming a power generation layer, and transport layer•electrode in which the electron acceptor and electron donor are mixed, a vapor deposition method, a coating method (including cast method and spin coating method) can be exemplified. Among them, the vapor deposition method and coating method (including cast method and spin coating method) can be exemplified as a method for forming a power generation layer. For producing an element having high photoelectric conversion efficiency by increasing the surface area in which the aforementioned holes and electrons are charge-separated, the coating method is preferred among them. The coating method is also excellent in terms of production speed.

The coating method used at that time is not limited, but the examples thereof include a spin coating method, a method of casting from solution, a dip coating method, a blade coating method, a wire bar coating method, a gravure coating method, and a spray coating method or the like. Further, it is also possible to perform patterning using a printing method such as an ink jet method, a screen printing method, an anastatic printing method, an intaglio printing method, an off-set printing method, or a flexo printing method.

After the coating, it is preferable to perform heating to remove residual solvents, moisture, or gas, to increase the mobility based on crystallization of a semiconductor material, or to have longer absorption wavelength. When an annealing treatment at a predetermined temperature is carried out during the production process, partial aggregation or crystallization is microscopically promoted so that the power generation layer can be prepared to have a suitable phase separation structure. As a result, the carrier mobility of the power generation layer is improved and high efficiency can be obtained.

The power generation layer (bulk heterojunction layer) may have a configuration in which the p-type organic semiconductor and the n-type organic semiconductor are mixedly present. However, it may also have a gradation configuration with a plurality of layers or mixing ratio in which each of their mixing ratio is different in the film thickness direction. The mixing ratio between the p-type organic semiconductor and the n-type organic semiconductor is preferably as follows; p-type organic semiconductor: n-type organic semiconductor=2:8 to 8:2.

(Other Functional Layers)

For the purpose of enhancing the utilization ratio of sun light (i.e., photoelectric conversion ratio), it is also possible to have a configuration of a back contact type organic photoelectric conversion element in which an element is formed on top of a pair of comb-like electrodes instead of the sandwich structure between the first electrode and the second electrode as shown in FIG. 1.

Further, although it is not illustrated in FIG. 1, for the purpose of enhancing the photoelectric conversion efficiency or enhancing the lifetime of an element, it is possible to have a configuration in which various intermediate layers are included in an element. Examples of the intermediate layer include a hole injection layer, an electron injection layer, an exciton blocking layer, an UV absorbing layer, a light reflection layer, a wavelength conversion layer, and a smoothing layer.

When a metallic material is used as a conductive material of a counter electrode, the light received at the counter electrode side is reflected to the first electrode side, and the light becomes re-usable and re-absorbed in the power generation layer. Thus, it is desirable in that the photoelectric conversion efficiency is improved more.

(Patterning)

The method or process for patterning the electrode, power generation layer, hole transport layer, electron transport layer, blocking layer, or the like according to the present invention is not particularly limited, and a well-known method can be suitably applied.

For a soluble material like a power generation layer, a transport layer, or the like, only an unnecessary part can be cleaned off after coating the entire surface by die coating or dip coating, or patterning can be performed by ablation using carbonate laser after forming a film or by direct cutting using a scriber. Further, it is also possible to perform direct patterning using various printing methods such as an ink jet method, a screen printing, or gravure printing.

For an insoluble material like an electrode material, a pattern can be formed by a vacuum vapor deposition method or a vacuum sputtering method, a plasma CVD method, various printing methods such as a screen printing method, a gravure printing method, or an ink jet method which uses an ink containing microparticles of the electrode material dispersed therein, a well-known method performing etching or lifting-off against the vapor deposited film, or by transferring a pattern which has been formed on another substrate.

(Sealing)

In order to avoid degradation of the produced organic photoelectric conversion element by oxygen, moisture, or the like in air, it is preferable to seal it by a well-known method. Examples of the method include a sealing method by adhering a cap made of aluminum or glass using adhesives, a method of attaching a plastic film formed with a gas barrier layer such as aluminum, silicon oxide, or aluminum oxide, to an organic photoelectric conversion element using adhesives, a method of coating with an organic polymer material having a high gas barrier property (such as polyvinyl alcohol), a method of precipitating an inorganic thin film (such as silicon oxide and aluminum oxide) or an organic film (such as parylene) having a high gas barrier property under vacuum, and a method of laminating them in combination.

Further, according to the present invention, from the viewpoint of enhancing the energy conversion efficiency and lifetime of an element, it may have a configuration in which the entire element is sealed with two pieces of a barrier-adhered substrate. According to the present invention, it is more preferably a configuration in which a moisture getter, an oxygen getter, or the like are also enclosed.

EXAMPLES

Hereinbelow, the present invention is explained in view of the examples, but the present invention is not limited to them.

[Preparation of p-Type Organic Semiconductor Material]

For a p-type organic semiconductor material, monomer synthesis and polymerization of a polythiophene-carbazole-benzothiadiazole copolymer (PCDTBT) were performed according to Adv. Mater., vol. 19 (2007) p 2295. By purification according to Soxhlet extraction, p-type organic semiconductor material PCDTBT having a number average molecular weight Mn of 35,000 and PDI of 2.0 was obtained. The solubility parameter of the PCDTBT was 18.5.

Example 1

[Fabrication of organic photoelectric conversion element SC-101]

On a glass substrate, a thing precipitated with a transparent conductive film of indium tin oxide (ITO) at 150 nm (sheet resistance of 10 Ω/□) was subjected to patterning with a width of 20 mm using a common photolithography technique and wet type etching to form a first electrode. The first electrode with formed patterns was cleaned in order by ultrasonic cleaning using a surfactant and ultra pure water and ultrasonic cleaning using ultra pure water. After that, it was dried by nitrogen blowing and finally subjected to a UV ozone cleaning.

On top of the transparent electrode, 1% isopropanol solution containing polyethyleneimine and glycerol propoxylate triglycidyl ether dissolved in isopropanol (all manufactured by Sigma-Aldrich) was coated and dried for 10 minutes on a hot plate at 120° C. to form a hole blocking layer (electron transport layer).

Subsequently, a liquid in which the PCDTBT synthesized above and $PC_{60}BM$ (E100H manufactured by Frontier Carbon Corporation: 6,6-phenyl-$C_{61}$-butyric acid methyl ester (solubility parameter of 20.1)) were admixed with each other at 1:1 in o-dichlorobenzene such that the solid content is 3.0% by mass was prepared. It was then filtered through a filter and a film of power generation layer was formed on the aforementioned substrate such that the film thickness after drying is about 100 nm. Subsequently, a liquid containing 2 parts of Emulgen (0.1% by mass) manufactured by Kao Chemical Corporation, isopropanol, per 1 part of PEDOT-PSS (Clevios P 4083 •H.C., manufactured by Starck GmbH) consisting of a conductive polymer and polyanion was prepared, and coated such that the film thickness after drying is about 100 nm followed by drying. According to the heating treatment again for 10 minutes at 120° C., a film of hole transport layer was formed.

Meanwhile, all the processes described above were performed in atmospheric air.

Next, the substrate formed with the aforementioned series of functional layers was transferred to a chamber equipped with an apparatus for vacuum vapor deposition. After lowering the pressure within the apparatus for vacuum vapor deposition to $1 \times 10^{-4}$ Pa or lower, Ag metal was laminated to 200 nm at vapor deposition rate of 1.0 nm/second to form a second electrode. The obtained organic photoelectric conversion element SC-101 was transferred to a nitrogen chamber, and sealing was performed using cavity glass for sealing and an UV curable resin. As a result, an organic photoelectric conversion element SC-101 which has light receiving part with a size of about 5×20 mm was fabricated.

[Fabrication of Organic Photoelectric Conversion Element SC-102]

The organic photoelectric conversion element SC-102 was fabricated in the same manner as the fabrication of SC-101 except that the compound represented by compound E is added at 0.3% by mass as an antioxidant for forming a film of the power generation layer of the organic photoelectric conversion element SC-101.

[Fabrication of Organic Photoelectric Conversion Elements SC-103 to SC119]

The organic photoelectric conversion elements SC-103 to SC-119 were fabricated in the same manner as the fabrication of SC-101 except that the antioxidant types represented in Table 1 are added at 0.3% by mass as an antioxidant instead of the compound E for forming a film of the power generation layer of the organic photoelectric conversion element SC-101.

Herein, according to Hansen's solubility parameter, the solubility parameter (SP value) was calculated from SMILE equation using the solubility parameter simulation software HSPiP.

The calculated value of solubility parameter for each antioxidant is shown in Table 1.

[Chemical formula 20]

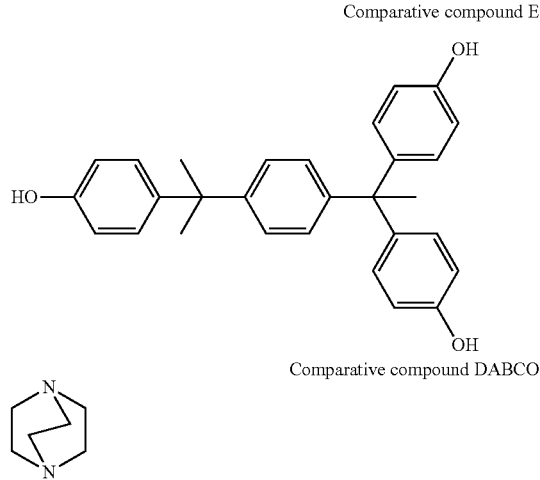

TABLE 1

| Type of antioxidant | Solubility parameter HSPiP |
|---|---|
| None | — |
| Comparative compound E | 23.6 |
| Comparative compound DABCO | 21.4 |
| Compound I-2 | 20.6 |
| Compound I-21 | 19.0 |
| Compound I-33 | 19.4 |
| Compound I-52 | 19.8 |
| Compound I-64 | 18.5 |

TABLE 1-continued

| Type of antioxidant | Solubility parameter HSPiP |
|---|---|
| Compound I-1 | 27.0 |
| Compound I-3 | 25.5 |
| Compound I-4 | 24.1 |
| Compound I-5 | 20.8 |
| Compound I-6 | 18.8 |
| Compound I-7 | 18.6 |
| Compound II-2 | 17.4 |
| Compound II-16 | 18.1 |
| Compound II-18 | 18.6 |
| Compound II-20 | 19.0 |
| Compound II-22 | 21.4 |

<<Evaluation of Performance of Element>>

The photoelectric conversion element produced in the above was irradiated with light with an intensity of 100 mW/cm² from a solar simulator (AM1.5G filter), and by overlapping a mask with effective area of 1 cm² on the light receiving part and evaluating the I-V characteristics, the short circuit current density Jsc (mA/cm²), open voltage Voc (V), and fill factor FF were obtained. Further, the photoelectric conversion efficiency η was obtained by the mathematical formula 2 and the results are shown in Table 2.

Photoelectric conversion efficiency η=$Jsc(mA/cm^2)\times Voc(V)\times FF(\%)$/Intensity of incident light(mW/cm²)    (Mathematical formula 2)

<<Evaluation of Lifetime of Element>>

With regard to the photoelectric conversion element fabricated in the above, the short circuit current density Jsc after light irradiation for 1000 hours was measured according to the evaluation of element performance described above using two-wavelength type white LED (small SMD manufactured by TOSHIBA CORPORATION) on a hot plate at 85° C. and after adjusting the light amount of LED to a value (about 1 Sun) almost identical to the short circuit current density Jsc which was measured for the evaluation of the element performance. Then, the ratio of Jsc after degradation relative to the initial Jsc was obtained, and it was also shown in Table 2.

TABLE 2

| Organic photoelectric conversion element | Type of antioxidant | Solubility parameter HSPiP | Photoelectric conversion efficiency η | Evaluation of lifetime of element 85° C. 1Sun 1000 h | Remarks |
|---|---|---|---|---|---|
| SC-101 | None | — | 4.5% | 38% | Comparative example |
| SC-102 | Comparative compound E | 23.6 | 3.2% | 71% | Comparative example |
| SC-103 | Comparative compound DABCO | 21.4 | 4.2% | 60% | Comparative example |
| SC-104 | Compound I-2 | 20.6 | 4.5% | 81% | Present invention |
| SC-105 | Compound I-21 | 19.0 | 4.3% | 78% | Present invention |
| SC-106 | Compound I-33 | 19.4 | 4.4% | 74% | Present invention |
| SC-107 | Compound I-52 | 19.8 | 4.6% | 75% | Present invention |
| SC-108 | Compound I-64 | 18.5 | 3.6% | 72% | Present invention |
| SC-109 | Compound I-1 | 27.0 | 2.8% | 75% | Present invention |
| SC-110 | Compound I-3 | 25.5 | 3.1% | 75% | Present invention |
| SC-111 | Compound I-4 | 24.1 | 3.4% | 75% | Present invention |
| SC-112 | Compound I-5 | 20.8 | 4.7% | 75% | Present invention |
| SC-113 | Compound I-6 | 18.8 | 3.4% | 75% | Present invention |
| SC-114 | Compound I-7 | 18.6 | 3.8% | 75% | Present invention |
| SC-115 | Compound II-2 | 17.4 | 3.1% | 92% | Present invention |
| SC-116 | Compound II-16 | 18.1 | 3.7% | 82% | Present invention |
| SC-117 | Compound II-18 | 18.6 | 3.3% | 81% | Present invention |
| SC-118 | Compound II-20 | 19.0 | 4.5% | 76% | Present invention |
| SC-119 | Compound II-22 | 21.4 | 4.2% | 80% | Present invention |

As clearly shown in Table 2, by adding the antioxidant according to the present invention to a power generation layer, a decrease in initial efficiency is suppressed and also a favorable effect is obtained against the Jsc attenuation caused by irradiation of light, and thus it was possible to obtain an effect of improving the lifetime of the photoelectric conversion element. Meanwhile, the present application is based on Japanese Patent Application No. 2011-173672 filed on Aug. 9, 2011, and the disclosure thereof is herein entirely incorporated by reference.

REFERENCE SIGNS LIST

10 Organic photoelectric conversion element
11 Transparent substrate
12 Transparent first electrode
13 Second electrode
14 Power generation layer
14' First power generation layer
15 Charge recombination layer
16 Second power generation layer
17 Hole transport layer
18 Electron transport layer

The invention claimed is:

1. An organic photoelectric conversion element comprising:
a transparent first electrode;
a power generation layer having a p-type organic semiconductor material and an n-type organic semiconductor material; and
a second electrode disposed on a transparent substrate,
wherein the power generation layer is a bulk heterojunction power generation layer including the p-type organic semiconductor material and the n-type organic semiconductor material, and additionally comprising a compound represented by the following formula (I):

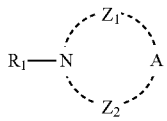

formula (I)

wherein $R_1$ represents a substituted or unsubstituted aryl group, $Z_1$ and $Z_2$ each represents a substituted or unsubstituted alkylene group having 1 to 3 carbon atoms, provided that a sum of the carbon atoms in the alkylene groups represented by $Z_1$ and $Z_2$ is 3 to 6; A represents an oxygen atom, N-$Z_3$, or S(O)$_{n5}$; $Z_3$ represents an alkyl group or an aryl group; and n5 represents an integer of from 0 to 2.

2. The organic photoelectric conversion element according to claim 1, wherein the compound represented by formula (I) is contained in an amount of 0.1 to 15 parts by mass with respect to 100 parts by mass of a sum of the p-type semiconductor and n-type semiconductor.

3. The organic photoelectric conversion element according to claim 1, wherein the compound represented by formula (I) has a solubility parameter value of 19 to 23.

4. An organic solar cell comprising the organic photoelectric conversion element according to claim 1.

5. An organic photoelectric conversion element comprising:
a transparent first electrode;
a power generation layer having a p-type organic semiconductor material and an n-type organic semiconductor material; and
a second electrode disposed on a transparent substrate,
wherein the power generation layer is a bulk heterojunction power generation layer including the p-type organic semiconductor material and the n-type organic semiconductor material, and additionally comprising a compound represented by one of the following formulas (I-A) to (I-E):

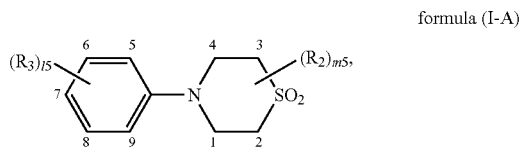

formula (I-A)

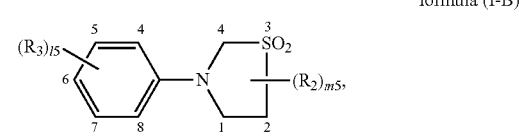

formula (I-B)

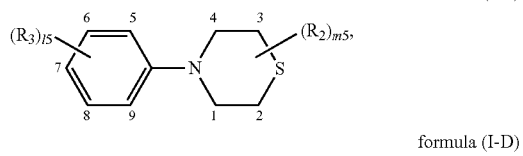

formula (I-C)

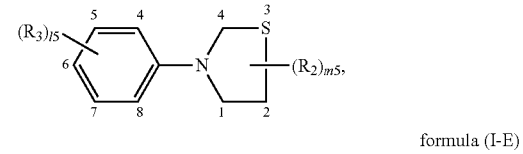

formula (I-D)

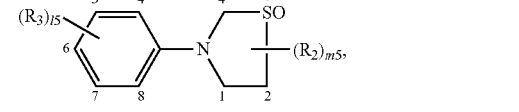

formula (I-E)

wherein $R_2$ and $R_3$ represent a halogen atom, a substituted or unsubstituted alkyl group (—$R_a$), a hydroxyalkyl group (—$R_a$(OH)), an alkoxy group (—O$R_a$), an aryloxy group, an amino group (—NH$_2$), an amino group (—NH$R_a$), an amino group (—N($R_a$)$_2$), a thioether group (—SRa), an ester group, —CO$R_a$, —COO$R_a$, —NHCO$R_a$, —NHCOO$R_a$, —NHSO$_2$$R_a$, or an alkylcarbonyloxy group (—OCO$R_a$), in which $R_a$ represents a substituted or unsubstituted alkyl group having 1 to 20 carbon atoms or a substituted or unsubstituted aryl group having 6 to 20 carbon atoms, and m5 and l5 each represent an integer of from 0 to 4.

6. The organic photoelectric conversion element according to claim 5, wherein the compound represented by one of the formulas (I-A) to (I-E) is contained in an amount of 0.1 to 15 parts by mass with respect to 100 parts by mass of a sum of the p-type semiconductor and n-type semiconductor.

7. The organic photoelectric conversion element according to claim 5, wherein the compound represented by one of the formulas (I-A) to (I-E) has a solubility parameter value of 19 to 23.

8. The organic photoelectric conversion element according to claim 5, wherein the compound represented by one of the formulas (I-A) to (I-E) is the compound of formula (I-A).

9. The organic photoelectric conversion element according to claim 5, wherein the compound represented by one of the formulas (I-A) to (I-E) is the compound of formula (I-B).

10. The organic photoelectric conversion element according to claim 5, wherein the compound represented by one of the formulas (I-A) to (I-E) is the compound of formula (I-C).

11. The organic photoelectric conversion element according to claim 5, wherein the compound represented by one of the formulas (I-A) to (I-E) is the compound of formula (I-D).

12. The organic photoelectric conversion element according to claim 5, wherein the compound represented by one of the formulas (I-A) to (I-E) is the compound of formula (I-E).

13. An organic solar cell comprising the organic conversion element according to claim 5.

* * * * *